United States Patent [19]

Schaper et al.

[11] Patent Number: 5,691,321
[45] Date of Patent: Nov. 25, 1997

[54] HETEROCYCLYLAMINO- AND HETEROCYCLYLOXY-CYCLOALKYL DERIVATIVES, THEIR PREPARATION, AND THEIR USE AS PESTICIDES AND FUNGICIDES

[75] Inventors: Wolfgang Schaper, Diedorf; Rainer Preuss, Berlin; Peter Braun, Nieder-Olm; Werner Knauf, Eppstein; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Berlin, Germany

[21] Appl. No.: 441,217

[22] Filed: May 15, 1995

[30] Foreign Application Priority Data

May 17, 1994 [DE] Germany ............. 44 17 163.3

[51] Int. Cl.⁶ ............. C07D 239/34; C07D 239/38; C07D 239/42; A01N 43/54
[52] U.S. Cl. ............. 514/63; 514/256; 514/269; 544/229; 544/319; 544/328; 544/329
[58] Field of Search ............. 544/319, 328, 544/329, 229; 514/256, 269, 63

[56] References Cited

U.S. PATENT DOCUMENTS

| | | |
|---|---|---|
| 4,435,402 | 3/1984 | Tsuji et al. ............. 424/251 |
| 4,895,849 | 1/1990 | Yoshioka et al. ............. 514/241 |
| 5,378,708 | 1/1995 | Drumm, III et al. ............. 514/256 |
| 5,397,781 | 3/1995 | Yanagibashi et al. ............. 514/256 |
| 5,439,911 | 8/1995 | Ohtsuka et al. ............. 514/256 |
| 5,525,724 | 6/1996 | Hunds ............. 544/334 |

FOREIGN PATENT DOCUMENTS

| | | |
|---|---|---|
| 0 057 440 | 11/1982 | European Pat. Off. . |
| 0 212 969 | 4/1987 | European Pat. Off. . |
| WO 93/00536 | 1/1993 | WIPO . |
| WO 93/19050 | 9/1993 | WIPO . |

Primary Examiner—Mukund J. Shah
Assistant Examiner—Deepak R. Rao
Attorney, Agent, or Firm—Curtis, Morris & Safford P.C.

[57] ABSTRACT

Heterocyclylamino- and heterocyclyloxy-cycloalkyl derivatives, their preparation, and their use as pesticides and fungicides

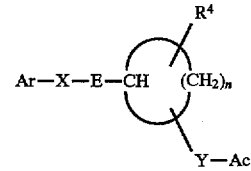

in which Ar is optionally substituted 4-pyridyl or 4-pyrimidinyl; X is NH, O or S; E is a bond or alkanediyl; n is 2–7; $R^4$ is H or alkyl, Y is O or a bond; and Ac is acyl, and salts thereof. The invention furthermore relates to processes for their preparation, to compositions comprising them, and to their use as pesticides and fungicides.

16 Claims, No Drawings

HETEROCYCLYLAMINO- AND HETEROCYCLYLOXY-CYCLOALKYL DERIVATIVES, THEIR PREPARATION, AND THEIR USE AS PESTICIDES AND FUNGICIDES

It has already been disclosed that certain 4-cycloalkylamino- and 4-cycloalkoxy-substituted nitrogen heterocycles have an insecticidal, acaricidal, ixodicidal and fungicidal activity (cf. WO 9300536).

There have been found novel 4-amino- and 4-alkoxy-substituted nitrogen heterocycles of the formula I

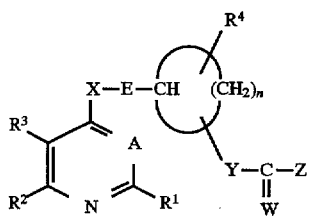

in which the radicals and groups are as defined below and which are highly suitable for controlling animal pests, such as insects, arachnids, nematodes, helminths and molluscs, for controlling endoparasites and ectoparasites in the field of veterinary medicine and for controlling fungal pests while being well tolerated by plants and having a favorable toxicity to warm-blooded species.

The invention therefore relates to compounds of the formula I in which $R^1$ is hydrogen, halogen, $(C_1-C_4)$-alkyl or $(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkyl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl, thiocyano, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkylsulfinyl, $(C_1-C_4)$-alkylsulfonyl or $(C_1-C_4)$-haloalkylsulfonyl;

$R^2$ and $R^3$ together with the carbon atoms to which they are bonded form an unsaturated 5- or 6-membered isocyclic ring which, if it is a 5-membered ring, can contain an oxygen or sulfur atom in place of $CH_2$, or which, if it is a 6-membered ring, can contain one or two nitrogen atoms in place of one or two CH units, this ring optionally being substituted by 1, 2 or 3 identical or different radicals and these radicals being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the carbon atoms to which they are bonded form a saturated 5-, 6- or 7-membered isocyclic ring which can contain oxygen and/or sulfur in place of one or two $CH_2$ groups and which is optionally substituted by 1, 2 or 3 $(C_1-C_4)$-alkyl groups;

A is CH or N;

X is NH, oxygen or sulfur;

E is a direct bond or a straight-chain or branched $(C_1-C_4)$-alkanediyl group, preferably a direct bond;

n is an integer from 2 to 7;

$R^4$ is hydrogen or $(C_1-C_4)$-alkyl;

Y is oxygen or a direct bond;

W is oxygen or sulfur, preferably oxygen;

Z is a radical $DR^5$ or $NR^5R^6$;

D is oxygen, sulfur or a direct bond, preferably oxygen or a direct bond;

$R^5$ and $R^6$ are identical or different and are hydrogen, alkyl, alkenyl, alkynyl, aryl or heterocyclyl, it being possible for the aryl or heterocyclyl radicals mentioned to be unsubstituted or to have attached to them up to three, in the case of fluorine also up to the maximum number of, identical or different radicals and it being possible for one or more, preferably up to three, nonadjacent saturated carbon units in the abovementioned alkyl, alkenyl or alkynyl radicals to be replaced by a carbonyl group or by hereto atom units, such as oxygen, $S(O)_x$, where x=0, 1 or 2, $NR^9$ or $SiR^7R^8$, $R^9$ being hydrogen, $(C_1-C_4)$-alkyl, $(C_1-C_4)$-alkoxy or $(C_1-C_4)$-alkanoyl and $R^7$ and $R^8$ being $(C_1-C_4)$-alkyl, preferably methyl; and in which moreover 3 to 12 atoms of these hydrocarbon radicals which are optionally modified as above can form a cycle and it is possible for these hydrocarbon radicals, with or without the abovementioned variations, to be optionally substituted by one or more, preferably up to three, in the case of fluorine up to the maximum number of, identical or different radicals selected from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocyclylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, with the proviso that, if the heterocycle in formula I is the pyridine system (A=CH, $R^2$ and $R^3$ not cyclically linked) and Z is the radical $DR^5$, $R^5$ is not $(C_1-C_4)$-alkyl, $R^5$ and $R^6$ form a ring system of the formula II or III

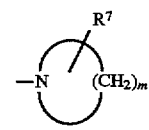

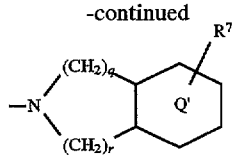

in which
the six-membered ring Q' is saturated or aromatic;
m is an integer from 2 to 7;
q and r are zero or integers whose total is a number from 2 to 4 and in which one CH$_2$ unit is optionally replaced by oxygen, sulfur or a group NR$^{10}$, and
R$^7$ and R$^{10}$ are identical or different and are in each case hydrogen, alkyl, haloalkyl, alkoxy, alkylthio, phenylalkyl or phenyl and the phenyl groups can be unsubstituted or have attached to them up to three, in the case of fluorine also up to the maximum number of, identical or different substituents,
and their salts, preferably acid addition salts,
in particular those compounds in which
R$^5$ and R$^6$ are hydrogen, (C$_1$-C$_{20}$)-alkyl, (C$_2$-C$_{20}$)-alkenyl, (C$_2$-C$_{20}$)-alkynyl, aryl, heterocyclyl, and, in the event that U is a direct bond, moreover hydroxyl, cyano, thiocyano, nitro or halogen, it being possible for the aryl or heterocyclyl radicals mentioned to be unsubstituted or to have attached to them up to three, in the case of fluorine also up to the maximum number of, identical or different radicals and it being possible for one or more, preferably up to three, nonadjacent saturated carbon units in the abovementioned alkyl, alkenyl or alkynyl radicals to be replaced by a carbonyl group or by hetero atom units, such as oxygen, S(O)$_x$, where x is 0, 1 or 2, NR$^9$ or SiR$^7$R$^8$, R$^9$ being hydrogen, (C$_1$-C$_4$)-alkyl, (C$_1$-C$_4$)-alkoxy or (C$_1$-C$_4$)-alkanoyl and R$^7$ and R$^8$ being (C$_1$-C$_4$)-alkyl, preferably methyl, and in which furthermore 3 to 12 atoms of these hydrocarbon radicals which are optionally modified as above can form a cycle and it is possible for these hydrocarbon radicals, with or without the abovementioned variations, to be optionally substituted by one or more, preferably up to three, in the case of halogen up to the maximum number of, identical or different radicals selected from the series consisting of halogen, aryl, aryloxy, arylthio, (C$_3$-C$_8$)-cycloalkoxy, (C$_3$-C$_8$)-cycloalkylthio, heterocyclyl, heterocyclyloxy, heterocyclylthio, (C$_1$-C$_{20}$)-alkanoyl, (C$_3$-C$_8$)-cycloalkanoyl, (C$_1$-C$_{20}$)-haloalkanoyl, aroyl, aryl-(C$_1$-C$_4$)-alkanoyl, (C$_3$-C$_8$)-cycloalkyl-(C$_1$-C$_4$)-alkanoyl, heterocyclyl-(C$_1$-C$_4$)-alkanoyl, (C$_1$-C$_{20}$)-alkoxycarbonyl, (C$_1$-C$_{20}$)-haloalkoxycarbonyl, (C$_3$-C$_8$)-cycloalkoxycarbonyl, (C$_3$-C$_8$)-cycloalkyl-(C$_1$-C$_4$)-alkoxycarbonyl, aryl-(C$_1$-C$_4$)-alkoxycarbonyl, heterocyclyl-(C$_1$-C$_4$)-alkoxycarbonyl, aryloxycarbonyl, heterocyclyloxlcarbonyl, (C$_1$-C$_{20}$)-alkanoyloxy, (C$_2$-C$_{20}$)-haloalkanoylalkoxy, (C$_3$-C$_8$)-cycloalkanoyloxy, (C$_3$-C$_8$)-cycloalkyl-(C$_1$-C$_4$)-alkanoyloxy, aroyloxy, aryl-(C$_1$-C$_4$)-alkanoyloxy, heterocyclyl-(C$_1$-C$_4$)-alkanoyloxy, (C$_1$-C$_{20}$)-alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, R$^5$ and R$^6$ form a ring system of the formula II or III
in which
the six-membered ring Q' is saturated or aromatic;
m is an integer from 2 to 7;
q and r are integers whose total is a number from 2 to 4 and in which one CH$_2$ unit can optionally be replaced by oxygen, sulfur or a group NR$^{10}$, and
R$^7$ and R$^8$ are identical or different and are in each case hydrogen, (C$_1$-C$_8$)-alkyl, (C$_1$-C$_4$)-haloalkyl, (C$_1$-C$_4$)-alkoxy, (C$_1$-C$_4$)-alkylthio, phenyl-(C$_1$-C$_4$)-alkyl or phenyl, it being possible for the phenyl groups to be unsubstituted or to have attached to them up to three, in the case of fluorine also up to the maximum number of, identical or different substituents, these substituents preferably being selected from the group consisting of (C$_1$-C$_4$)-alkyl, (C$_1$-C$_4$)-haloalkyl, (C$_1$-C$_4$)-alkoxy, (C$_1$-C$_4$)-haloalkoxy, (C$_1$-C$_4$)-alkylthio and halogen;
and furthermore, in the event that n is the number 5 and E is a direct bond, the groups —X—E and

are preferably in the cis position relative to each other and assume positions 1 and 4 on the cyclohexane ring.
Other preferred compounds of the formula I are those in which
R$^1$ is hydrogen;
R$^2$ is (C$_1$-C$_4$)-alkyl, cyclopropyl, (C$_1$-C$_4$)-haloalkyl or methoxymethyl;
R$^3$ is hydrogen, methyl, ethyl, methoxy, ethoxy, halogen or cyano; or
R$^2$ and R$^3$ together with the carbon atoms to which they are bonded form an unsaturated 5- or 6-membered ring which, in the case of the 5-membered ring, can contain a sulfur atom in place of a CH$_2$ unit, or R$^2$ and R$^3$ together with the carbon atoms to which they are bonded form a saturated 5- or 6-membered ring which can contain a sulfur or an oxygen atom in place of one CH$_2$ unit;
A is CH or N;
X is NH or oxygen;
E is a direct bond;
R$^4$ is hydrogen or (C$_1$-C$_4$)-alkyl;
Y is oxygen or a direct bond;
W is oxygen;
Z is a radical DR$^5$ or NR$^5$R$^6$; and
D is oxygen or a direct bond;
in particular those compounds in which
R$^2$ is (C$_1$-C$_3$)-alkyl, cyclopropyl, trifluoromethyl or methoxymethyl;
R$^3$ is methyl, ethyl, methoxy, halogen or cyano; or
R$^2$ and R$^3$ together with the carbon atoms to which they are bonded form the quinazoline or quinoline system; or
R$^2$ and R$^3$ together with the carbon atoms to which they are bonded form a saturated 6-membered ring which can contain an oxygen or sulfur atom and
Z is a radical DR$^5$ or NR$^5$R$^6$; particularly preferred compounds of the formula I are those in which
R$^1$ is hydrogen;
R$^2$ is ethyl, propyl, isopropyl or methoxymethyl;

$R^3$ is fluorine, chlorine, bromine or methoxy; or $R^2$ and $R^3$ together with the carbon atom to which they are bonded form the quinazoline system which can be substituted by fluorine, chlorine, bromine and/or methyl; or $R^2$ and $R^3$ together with the pyrimidine ring form the 5,6,7,8-tetrahydroquinazoline system, A is CH or N;

X is NH;

E is a direct bond;

$R^4$ is hydrogen;

n is the number 4 or 5;

Y is oxygen or a direct bond;

Z is $DR^5$ or $NR^5R^6$;

D is oxygen or a direct bond, and

W is oxygen.

Very particularly preferred compounds of the formula I are those in which $R^1$ is hydrogen;

$R^2$ is methoxymethyl and $R^3$ is methoxy or chlorine; or $R^2$ is ethyl, propyl or isopropyl and $R^3$ is chlorine or bromine; or $R^2$ and $R^3$ together with the carbon atom to which they are bonded form the quinazoline system;

A is CH or N;

X is NH;

E is a direct bond;

$R^4$ is hydrogen;

n is the number 4 or 5;

Y is a direct bond;

Z is $DR^5$ or $NR^5R^6$;

D is oxygen or a direct bond, and

W is oxygen.

Most preferred amongst these are compounds of the formula I in which $R^1$ is hydrogen;

$R^2$ is methoxymethyl and $R^3$ is methoxy; or $R^2$ is ethyl and $R^3$ is chlorine or bromine; or $R^2$ and $R^3$ together with the carbon atoms to which they are bonded form the quinazoline systems A is nitrogen;

X is NH;

E is a direct bond;

$R^4$ is hydrogen;

n is the number 5 and the radicals are in the 1,4-position and in the cis-position relative to each others Y is a direct bond;

W is oxygen;

Z is $DR^5$;

D is oxygen or a direct bond; and $DR^5$ groups which are emphasized being those in which $R^5$ is hydrogen, $(C_1-C_{12})$-alkyl, $(C_3-C_8)$-cycloalkyl, $(C_3-C_8)$-cycloalkyl -$(C_1-C_4)$-alkyl, $(C_1-C_4)$-alkyl -$(C_3-C_8)$-cycloalkyl, phenyl or phenyl-$(C_1-C_4)$-alkyl, it being possible for the phenyl radicals to be unsubstituted or substituted as indicated above for $R^5$=aryl; or Z is $NR^5R^6$ and $R^5$ in this case is preferably $(C_1-C_4)$-alkyl and $R^6$ in this case is preferably $(C_1-C_{12})$-alkyl, $(C_3-C_8)$-cycloalkyl, phenyl or phenyl-$(C_1-C_4)$-alkyl, it being possible for the phenyl radicals to be unsubstituted or substituted as indicated above in the case of $R^6$=aryl, or it being possible for $R^5$ and $R^6$ to form a ring system of the formula II or III.

In the above formula, "halogen" is to be understood as meaning a fluorine, chlorine, bromine or iodine atom, preferably a fluorine, chlorine or bromine atom;

the term "$(C_1-C_4)$-alkyl" as meaning an unbranched or branched hydrocarbon radical having 1–4 carbon atoms, such as, for example, the methyl, ethyl, propyl, isopropyl, 1-butyl, 2-butyl, 2-methylpropyl or tert-butyl radical;

the term "$(C_1-C_{20})$-alkyl" as meaning the abovementioned alkyl radicals, such as, for example, the pentyl, 2-methylbutyl or 1,1-dimethylpropyl radical, or the hexyl, heptyl, octyl, 1,3,3-tetramethylbutyl, nonyl, 1-decyl, 2-decyl, undecyl, dodecyl, pentadecyl or eicosyl radical; the term "$(C_1-C_4)$-haloalkyl" as meaning an alkyl group mentioned under the term "$(C_1-C_4)$-alkyl" in which one or more hydrogen atoms are replaced by the abovementioned halogen atoms, preferably chlorine or fluorine, such as, for example, the trifluoromethyl group, the 1-fluoroethyl group, the 2,2, 2-trifluoroethyl group, the chloromethyl or fluoromethyl group, the difluoromethyl group or the 1,1,2,2-tetrafluoroethyl group;

the term "$(C_1-C_2)$-fluoroalkyl" is to be understood as meaning, for example, the 1-fluoroethyl, 2-fluoroethyl, 1,1-difluoroethyl or 2,2,2-trifluoroethyl group;

the term "cycloalkyl" is to be understood as preferably meaning $(C_3-C_8)$-cycloalkyl;

the term "cycloalkoxy" as preferably meaning $(C_3-C_8)$-cycloalkoxy;

the term "cycloalkylthio" as preferably meaning $(C_3-C_8)$-cycloalkylthio;

the term "$(C_3-C_5)$-cycloalkyl" as meaning the cyclopropyl, cyclobutyl or cyclopentyl group;

the term "$(C_3-C_8)$-cycloalkyl" as meaning the radicals mentioned above under $(C_3-C_5)$-cycloalkyl, such as the cyclohexyl, cycloheptyl or cyclooctyl radical;

the term "$(C_3-C_5)$-halocycloalkyl" as meaning one of the abovementioned $(C_3-C_5)$-cycloalkyl radicals in which one or more, in the case of fluorine optionally also all, hydrogen atoms are replaced by halogen, preferably fluorine or chlorine, such as, for example, the 2,2-difluoro or 2,2-dichlorocyclopropane group or the fluorocyclopentane radical;

the term "$(C_2-C_4)$-alkenyl" as meaning, for example, the vinyl, allyl, 2-methyl-2-propenyl or 2-butenyl group;

the term "$(C_2-C_{20})$-alkenyl" as meaning the radicals mentioned above as well as, for example, the 2-pentenyl, 2-decenyl or the 2-eicosenyl group;

the term "$(C_2-C_4)$-haloalkenyl" as meaning a $(C_2-C_4)$-alkenyl group in which the hydrogen atoms are partially, or, in the case of fluorine also fully, replaced by halogen, preferably fluorine or chlorine;

the term "$(C_2-C_4)$-alkynyl" as meaning, for example, the ethynyl, propargyl, 2-methyl-2-propynyl or 2-butynyl group;

the term "$(C_2-C_{20})$-alkynyl" as meaning the radicals mentioned above as well as, for example, the 2-pentynyl or 2-decynyl group;

the term "$(C_2-C_4)$-haloalkynyl" as meaning a $(C_2-C_4)$-alkynyl group in which the hydrogen atoms are partially, in the case of fluorine also fully, replaced by halogen atoms, preferably fluorine or chlorine; the term "($C_1$–$C_4$)-hydroxyalkyl" as meaning, for example, the hydroxymethyl, 1-hydroxyethyl, 2-hydroxyethyl, 1-hydroxy-1-methylethyl or the 1-hydroxypropyl group; the term "($C_1$–$C_4$)-alkanoyl" as meaning, for example, the formyl, acetyl, propionyl, 2-methylpropionyl or butyryl group;

the term "($C_1$–$C_4$)-haloalkanoyl" as meaning a ($C_1$–$C_4$)-alkanoyl group in which the hydrogen atoms are partially, in the case of fluorine also fully, replaced by halogen atoms, preferably fluorine or chlorine;

the term "cyano-($C_1$–$C_4$)-alkyl" as meaning a cyanoalkyl group whose hydrocarbon radical is as defined under the term "($C_1$–$C_4$)-alkyl";

the term "($C_1$–$C_4$)-alkoxycarboxyl" as meaning for example, the methoxycarbonyl, ethoxycarbonyl, propoxycarbonyl butoxycarbonyl or tert-butoxycarbonyl group;

the term "($C_1$–$C_{12}$)-alkoxycarbonyl" as meaning the abovementioned radicals as well as, for example, the hexyloxycarbonyl, 2-methylhexyloxycarbonyl, decyloxycarbonyl or dodecyloxycarbonyl group;

the term "($C_1$–$C_4$)-haloalkoxycarbonyl" as meaning a ($C_1$–$C_4$)-alkoxycarbonyl group in which one or more, in the case of fluorine, if appropriate, also all, hydrogen atoms are replaced by halogen, preferably fluorine or chlorine;

the term "($C_1$–$C_4$)-alkylthio" an alkylthio group whose hydrocarbon radical is as defined under the term "($C_1$–$C_4$)-alkyl";

the term "($C_1$–$C_4$)-haloalkylthio" as meaning a ($C_1$–$C_4$)-alkylthio group in which one or more, in the case of fluorine, if appropriate, also all, hydrogen atoms of the hydrocarbon moiety are replaced by halogen, in particular chlorine or fluorine;

the term "fluoromethyl" as meaning the mono-, di- and trifluoromethylthio group;

the term "($C_1$–$C_4$)-alkylsulfinyl" as meaning, for example, the methyl-, ethyl-, propyl-, isopropyl-, butyl-, isobutyl-, sec-butyl- or tert-butylsulfinyl group;

the term "($C_1$–$C_4$)-alkylsulfonyl" as meaning, for example, the methyl-, ethyl-, propyl-, isopropyl-, butyl-, isobutyl-, sec-butyl- or tert-butylsulfonyl group;

the terms "($C_1$–$C_4$)-haloalkylsulfinyl" and "($C_1$–$C_4$)-haloalkylsulfonyl" as meaning ($C_1$–$C_4$)-alkylsulfinyl and -sulfonyl radicals having the abovementioned meanings, in which one or more, in the case of fluorine, if appropriate, also all, hydrogen atoms of the hydrocarbon moiety are replaced by halogen, in particular chlorine or fluorine;

the terms ""fluoromethylsulfinyl" and "fluoromethylsulfonyl" as meaning the mono-, di- and trifluoromethylsulfinyl and -sulfonyl group;

the term "($C_1$–$C_4$)-alkoxy" as meaning an alkoxy group whose hydrocarbon radical is as defined under the term "($C_1$–$C_4$)-alkyl";

the term "($C_1$–$C_4$)-haloalkoxy" as meaning a haloalkoxy group whose halohydrocarbon radical is as defined under the term "($C_1$–$C_4$)-haloalkyl";

the term "($C_1$–$C_4$)-alkoxy-($C_1$–$C_4$)-alkyl" as meaning, for example, a 1-methoxyethyl group, a 2-methoxyethyl group, a 2-ethoxyethyl group, a methoxymethyl or ethoxymethyl group, a 3-methoxypropyl group or a 4-butoxybutyl group;

the terms "($C_1$–$C_4$)-haloalkoxy-($C_1$–$C_4$)-alkyl", "($C_1$–$C_4$)-alkoxy-($C_1$–$C_4$)-haloalkyl" and "($C_1$–$C_4$)-haloalkoxy-($C_1$–$C_4$)-haloalkyl" as meaning ($C_1$–$C_4$)-alkoxy-($C_1$–$C_4$)-alkyl radicals as defined above, in which one or more, in the case of fluorine, if appropriate, also all, hydrogen atoms of the relevant hydrocarbon moieties are replaced by halogen, preferably chlorine or fluorine;

the term "($C_1$–$C_4$)-alkylthio-($C_1$–$C_4$)-alkyl" as meaning, for example, methylthiomethyl, ethylthiomethyl, propylthiomethyl, 2-methylthioethyl, 2-ethylthioethyl or 3-methylthiopropyl;

the term "aryl" as meaning an isocyclic aromatic radical having preferably 6 to 14, in particular 6 to 12, carbon atoms, such as, for example, phenyl, naphthyl or biphenylyl, preferably phenyl;

the term "heterocyclyl" as meaning a heteroaromatic or heteroaliphatic ring system, "heteroaromatic ring system" to be understood as meaning an aryl radical in which at least one CH group is replaced by N and/or at least two adjacent CH groups are replaced by S, NH or O, preferably a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and the term "heteroaliphatic ring system" as meaning a ($C_3$–$C_8$)-cycloalkyl radical in which at least one carbon unit is replaced by O, S or a group $NR^{11}$ and $R^{11}$ is hydrogen, ($C_1$–$C_4$)-alkyl, ($C_1$–$C_4$)-alkoxy or aryl;

the term "arylthio" as meaning, for example, the phenylthio or the 1- or 2-naphthylthio group;

the term "aryloxy" as meaning, for example, the phenoxy or 1- or 2-naphthyloxy groups the term "heterocyclyloxy" or "heterocyclylthio" as meaning one of the abovementioned heterocyclic radicals which are linked via an oxygen or sulfur atom;

the term "($C_3$–$C_8$)-cycloalkoxycarbonyl" as meaning, for example, the cyclobutyloxycarbonyl, cyclopentyloxycarbonyl, cyclohexyloxycarbonyl or cycloheptyloxycarbonyl group;

the term "($C_3$–$C_8$)-cycloalkyl-($C_1$–$C_4$)-alkoxycarbonyl" as meaning, for example, the cyclopropylmethoxycarbonyl, cyclobutylmethoxycarbonyl, cyclopentyloxymethylcarbonyl, cyclohexyloxymethylcarbonyl, 1-(cyclohexyl)-ethoxycarbonyl or the 2-(cyclohexyl)-ethoxycarbonyl group;

the term "aryl-($C_1$–$C_4$)-alkoxycarbonyl" as meaning, for example, the benzyloxycarbonyl, 1-naphthylmethoxycarbonyl, 2-naphthylmethoxycarbonyl, 1-phenyl-ethoxycarbonyl or the 2-phenyl-ethoxycarbonyl group;

the term "aryloxycarbonyl" as meaning, for example, the phenoxycarbonyl, naphthoxycarbonyl or the biphenyloxycarbonyl group;

the term "heterocyclyl-($C_1$–$C_4$)-alkanoyl" as meaning, for example, the thenoyl, furoyl, thienylacetyl or the pyridylacetyl groups the term "heterocyclyl-$(C_1-C_4)$-alkoxycarbonyl" as meaning, for example, the thienylmethoxycarbonyl, furylmethoxycarbonyl, pyridylmethoxycarbonyl or the thienylethoxycarbonyl group;

the term "$(C_1-C_{20})$-alkanoxyloxy" as meaning, for example, the formyloxy, acetoxy, propionyloxy, butyryloxy, pivaloyloxy, valeroyloxy or the hexanoyloxy group;

the term "$(C_2-C_{20})$-haloalkanoyloxy" as meaning a $(C_2-C_{20})$-alkanoyloxy group in which one or more, in the case of fluorine, if appropriate, also all, hydrogen atoms of the hydrocarbon moiety are replaced by halogen, in particular fluorine or chlorine;

the term "$(C_3-C_8)$-cycloalkanoyloxy" as meaning, for example, the cyclopropanoyloxy, cyclobutenoyloxy, cyclopentanoyloxy, cyclohexanoyloxy or the cycloheptanoyloxy group;

the term "$(C_3-C_8)$-cycloalkyl-$(C_1-C_4)$-alkanoyloxy, as meaning, for example, the cyclopropylcarbonyloxy, cyclopropylacetoxy, cyclobutylcarbonyloxy, cyclopentylcarbonyloxy, cyclohexylcarbonyloxy, cyclohexylacetoxy or the 4-cyclohexyl-butyryloxy group;

the term "aroyloxy" as meaning, for example, the benzoyloxy or the naphthoyloxy group;

the term "heterocyclyl-$(C_1-C_4)$-alkanoyloxy" as meaning, for example, the thienylcarbonyloxy, thienylacetoxy, pyridylcarbonyloxy or the pyrimidinylcarbonyloxy group; the term "aryl-$(C_1-C_4)$-alkanoyloxy" as meaning, for example, the benzoyloxy, naphthoyloxy or the phenylacetoxy group;

the term "$(C_1-C_{20})$-alkylsulfonyloxy" as meaning, for example, the methane-, ethane-, butane- or hexanesulfonyloxy group;

the term "arylsulfonyloxy" as meaning, for example, the phenylsulfonyloxy or the toluenesulfonyloxy group.

The substituents which the various aliphatic, aromatic and heterocyclic ring systems can have attached to them include, for example, halogen, $(C_1-C_4)$-alkyl, $(C_1-C_4)$-trialkylsilyl, $(C_1-C_4)$-haloalkyl, $(C_1-C_4)$-alkoxy, $(C_1-C_4)$-haloalkoxy, $(C_1-C_4)$-alkoxy-$(C_1-C_4)$, $(C_1-C_2)$-alkoxy-$[CH_2CH_2]_{1,2}$-ethoxy, $(C_1-C_4)$-alkylthio, $(C_1-C_4)$-alkylsulfinyl, $(C_1-C_4)$-alkylsulfonyl, phenyl, benzyl, phenoxy, halophenoxy, $(C_1-C_4)$-alkylphenoxy, $(C_1-C_4)$-alkoxyphenoxy, $(C_1-C_4)$-haloalkoxyphenoxy, $(C_1-C_4)$-haloalkylphenoxy, phenylthio, heterocyclyl, heterocyclylthio or heterocyclyloxy, it being possible for one or more, in the case of fluorine also up to the maximum number of hydrogen atoms in the alkyl radicals and the radicals derived therefrom to be replaced by halogen, preferably chlorine or fluorine.

Furthermore, the definition that it is possible for one or more, preferably up to three, nonadjacent saturated carbon units in the abovementioned alkyl, alkenyl or alkynyl radicals to be replaced by a carbonyl group or by hereto atom units, such as oxygen, $S(O)_x$, where $x=0$, 1 or 2, $NR^9$ or $SiR^7R^8$, $R^9$ being hydrogen, $(C_1-C_4)$-alkyl, $(C_1-C_4)$-alkoxy or $(C_1-C_4)$-alkanoyl and $R^7$ and $R^8$ being $(C_1-C_4)$-alkyl, preferably methyl;

and in which moreover 3 to 12 atoms of these hydrocarbon radicals which are optionally modified as above can form a cycle and it is possible for these hydrocarbon radicals, with or without the abovementioned variations, to be optionally substituted by one or more, preferably up to three, in the case of fluorine up to the maximum number of, identical or different radicals selected from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, alkanoyloxy, haloalkanoyloxy, cycloalkanoyloxy, cycloalkylalkanoyloxy, aroyloxy, arylalkanoyloxy, heterocyclylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents", is to be understood as meaning, for example, alkoxyalkyl radicals, such as, for example, the methoxymethyl, methoxyethyl or ethoxyethyl group; or alkoxyalkoxyalkyl radicals, such as, for example, the methoxy- or ethoxy-ethoxyethyl groups or alkylthioalkyl radicals, such as, for example, the methyl- or the ethylthioethyl group; or alkylsulfinylalkyl radicals, such as, for example, the methyl- or ethylsulfinylethyl groups or alkylsulfonylalkyl radicals, such as, for example, the methyl- or ethylsulfonylethyl group; or alkyldialkylsilylalkyl, preferably alkyldimethylsilylalkyl radicals, such as, for example, the trimethylsilylmethyl or the trimethylsilylethyl group; or trialkylsilyl, preferably alkyldimethylsilyl radicals, such as, for example, the trimethylsilyl, ethyldimethylsilyl, tert-butyldimethylsilyl or the octyldimethylsilyl group; or cycloalkyldialkylsilyl, preferably cycloalkyldimethylsilyl radicals, such as, for example, the cyclohexyldimethylsilyl group; or aryldialkylsilyl, preferably aryldimethylsilyl radicals, such as, for example, the phenyldimethylsilyl group; or arylalkyldialkylsilyl, preferably aryldimethylsilyl radicals, such as, for example, the benzyldimethylsilyl or the phenylethyldimethylsilyl group; or alkanoylalkyl radicals, such as, for example, the acetylmethyl or the pivaloylmethyl group; or cycloalkanoylalkyl radicals, such as, for example, the cyclopropylcarbonylmethyl or the cyclohexylcarbonylmethyl group; or haloalkanoylalkyl radicals such as, for example, the trifluoro- or trichloroacetylmethyl group; or aroylalkyl radicals, such as, for example, the benzoyl or naphthoylalkyl radicals, such as, for example, the phenylacetylmethyl group; or heterocyclylcarbonylalkyl radicals, such as, for example, the thienyl- or pyridylacetylmethyl group; or arylalkyl radicals, such as, for example, the benzyl, the 2-phenylethyl, the 1-phenylethyl, the 1-methyl-1-phenylethyl group, the 3-phenylpropyl, the 4-phenylbutyl group, the 2-methyl-2-phenylethyl group or the 1-methyl- or 2-methyl-naphthyl group; or heterocyclylalkyl radicals, such as, for example, the thienylmethyl, pyridylmethyl, furfuryl, tetrahydrofurfuryl, tetrahydropyranylmethyl or the 1,3-dioxalanyl-2-methyl group; or aryloxyalkyl radicals, such as, for example, the phenoxymethyl or naphthoxymethyl group; or cycloalkyl radicals, monocyclic, such as, for example, the cyclopropyl, cyclobutyl, cyclopentyl, cyclohexyl, cycloheptyl or cyclooctyl radical, bicyclic, such as, for example, the norbornyl radical or the bicyclo[2,2,2] octane radical, or condensed, such as the decahydronaphthyl radical;

alkylcycloalkyl radicals such as, for example, the 4-methyl- or the 4-tert-butylcyclohexyl group or the 1-methyl-cyclopropyl, -cyclobutyl, -cyclopentyl or -cyclohexyl group;

cyclohexylalkyl radicals, such as, for example, the cyclohexylmethyl or -ethyl groups or else haloalkyl derivatives of the corresponding groups, such as, for example, the haloalkyl, haloalkoxyalkyl, alkoxyhaloalkyl, haloalkylcycloalkyl or halocycloalkyl radicals.

The illustration given above applies analogously to radicals where the number of carbon atoms has not been mentioned specifically, as well as to homologs or radicals derived therefrom.

The present invention relates to the compounds of the formula I in the form of the free base or in the form of an acid addition salt. Acids which can be used for salt formation are inorganic acids, such as hydrochloric acid, hydrobromic acid, nitric acid, sulfuric acid, phosphoric acid or organic acids, such as formic acid, acetic acid, propionic acid, malonic acid, oxalic acid, fumaric acid, adipic acid, stearic acid, oleic acid, methanesulfonic acid, benzenesulfonic acid or toluenesulfonic acid.

Besides the abovementioned cis/trans isomers on the cycloalkyl group, some of the compounds of the formula I have one or more asymmetric carbon atoms or stereoisomers on double bonds. Enantiomers or diastereomers may therefore occur. The invention embraces the pure isomers as well as their mixtures. The diastereomer mixtures can be separated into the components by customary methods, for example by selective crystallization from suitable solvents or by chromatography. Racemates can be resolved into the enantiomers by customary methods, for example by salt formation with an optically active acid, separation of the diastereomeric salts and setting free the pure enantiomers by means of a base.

The invention furthermore relates to a process for the preparation of compounds of the formula I, which comprises reacting a compound of the formula IV

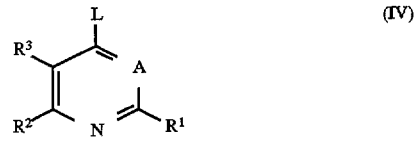

in which A, $R^1$, $R^2$ and $R^3$ are as defined under formula I and L is a leaving group, for example halogen, alkylthio, alkanesulfonyloxy or arylsulfonyloxy, alkylsulfonyl or arylsulfonyl, with a nucleophile of the formula V

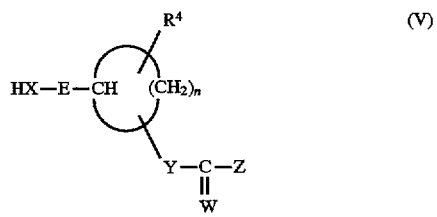

in which X, E, $R^4$, n, Y, W and Z are as defined under formula I, and, in the event that $R^3$ is hydrogen, halogenating, preferably chlorinating or brominating, the compounds of the formula I obtained by this route or by a different route in the 5 position of the heterocycle, if so desired.

The substitution reaction described above is known in principle. The leaving group Z can be varied within wide limits and can be, for example, a halogen atom, such as fluorine, chlorine, bromine or iodine, or alkylthio, such as methylthio or ethylthio, or alkanesulfonyloxy, such as methane-, trifluoromethane- or ethanesulfonyloxy, or arylsulfonyloxy, such as benzenesulfonyloxy or toluenesulfonyloxy, or alkylsulfonyl, such as methyl- or ethylsulfonyl, or arylsulfonyl, such as phenyl- or toluenesulfonyl.

The abovementioned reaction is carried out in a temperature range of 20°–150° C., expediently in the presence of a base and, if appropriate, in an inert organic solvent such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. Mixtures of the abovementioned solvents can also be used.

In the event that X is oxygen, examples of suitable bases are carbonates, hydrogencarbonates, amides or hydrides of alkali metals or alkaline earth metals, such as sodium carbonate, sodium hydrogencarbonate, potassium carbonate, sodium amide or sodium hydride, and in the event that X is NH, examples are carbonates, hydrogencarbonates, hydroxides, amides or hydrides of alkali metals or alkaline earth metals, such as sodium carbonate, sodium hydrogencarbonate, potassium carbonate, sodium hydroxide, sodium amide or sodium hydride, or organic bases such as triethylamine or pyridine. A second equivalent of an amine V can also be employed as auxiliary base.

The invention furthermore relates to a process for the preparation of compounds of the formula I, in which n is the number 5, in particular pyridine derivatives where E is a direct bond, which comprises reacting a compound of the formula IV with a nucleophile of the formula VI to give a compound of the formula VII, from which the compounds I are obtained by hydrogenating the phenyl radical.

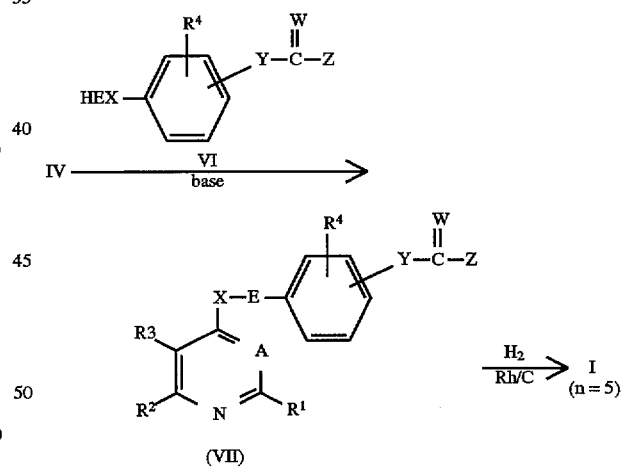

The reaction to give the compounds VII is carried out analogously to the synthesis of the compounds of the formula I from educts IV and V. VII is hydrogenated by known methods (cf., for example, F. Zymalkowski, Katalytische Hydrierungen [Catalytic Hydrogenations], p. 191, Enke Verlag, Stuttgart, 1965) and results in cis/trans mixtures on the cyclohexyl side chain, which can be separated by crystallization or chromatography.

The invention furthermore relates to a process for the preparation of compounds of the formula I in which X is NH, in particular pyridine derivatives, which comprises reacting a compound of the formula VIII in which $R^1$, $R^2$, $R^3$ and A are as defined above with an alkylating agent of the formula IX in which E, n, $R^4$, Y, W and z are as defined for formula I and L is a leaving group defined as for formula IV, to give a compound of the formula X and subsequently converting the latter into the compounds of the formula I by means of reduction.

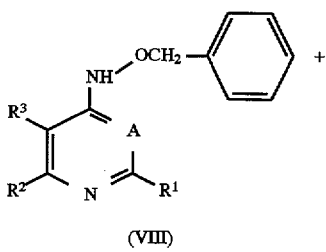

(VIII)

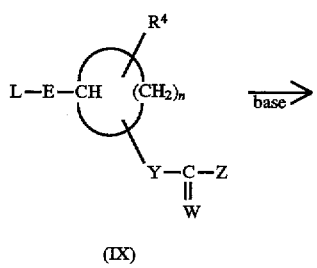

(IX)

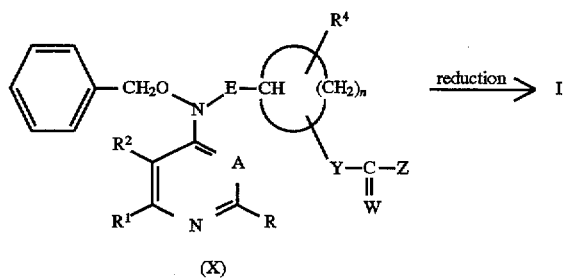

(X)

The alkylation to give the compounds of the formula X is carried out analogously to the synthesis of the compounds of the formula I from the compounds of the formula IV. The reductive cleavage of the intermediates X is carried out analogously to known methods (cf. R. Huisgen et al. B. 101, 2559 (1968), C. H. Rayburn, W. R. Harlau, H. R. Haumer Am. Soc. 72, 1721 (1950)). The preparation of the educts VIII is described in DOS 4 331 179.

The invention furthermore relates to a process for the preparation of compounds of the formula I in which A is CH and $R^2$ and $R^3$ together with the carbon atoms to which they are bonded form a saturated 6-membered ring (5,6,7,8-tetrahydroquinolines), which comprises hydrogenating a compound of the formula I in which A is CH and $R^2$ and $R^3$ together with the carbon atoms to which they are bonded form an unsaturated 6-membered ring (quinolines) in the presence of a noble metal catalyst.

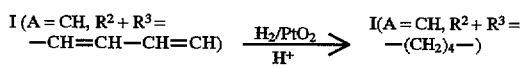

The hydrogenation is carried out analogously to known methods (cf. J. Z. Ginos, J. Org. Chem. 40, 1191, (1975)).

The invention furthermore relates to a process for the preparation of compounds of the formula I in which Y is oxygen, which comprises reducing a compound of the formula XI

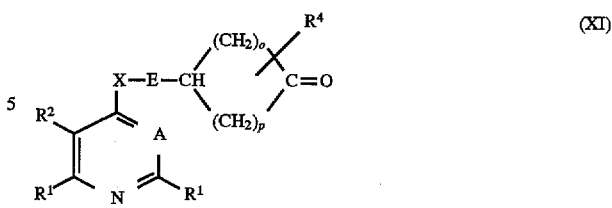

in which A, $R^1$, $R^2$, $R^3$, $R^4$, X and E are as defined for formula I and the total of the indices o and p equals the number (n-1), n being defined as for formula I, with a suitable reducing agent to give a compound of the formula XII

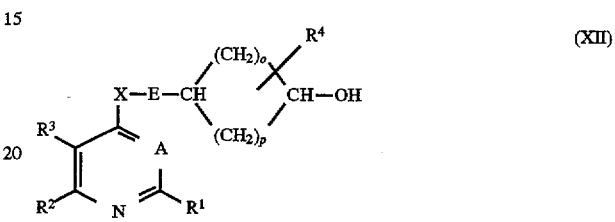

in which $R^1$, $R^2$, $R^3$, $R^4$, E and A are as defined for formula I and o and p are as defined for formula XI, and subsequently acylating this compound of the formula XII on the OH group with an acylating agent of the formula

in which W and Z are as defined for formula I and L is a leaving group as defined for formula IV.

The reduction of the compounds XI to give the compounds XII is carried out analogously to known processes. Preferred reducing agents are complex hydrides such as lithium aluminum hydride, sodium borohydride and, in the case of the cyclohexyl derivatives, complex hydrides which have voluminous substituents on the central atom, such as, for example, lithium tri-sec-butyl borohydride (L-Selectride®) or lithium trisiamyl borohydride (LS-Selectride®), which give, upon reduction, the preferred derivatives in the cis configuration with regard to the 1,4-substituents.

The subsequent acylation reaction is carried out analogously to known methods for esterifying alcohols with activated carboxylic acid derivatives, for example by reacting the compounds XII with a carboxylic acid chloride

in an inert solvent, such as dichloroethane, trichloroethane, ether or tetrahydrofuran, in the presence of a base, such as, for example, triethylamine or pyridine, or else using the base itself (pyridine) as the solvent.

The invention furthermore relates to a process for the preparation of intermediates of the formula XII, which comprises reacting a compound of the formula IV with a nucleophile of the formula XIII

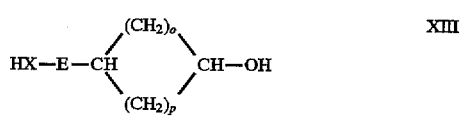

in which X, E, o and p are as defined for formula XIII. The reaction is carried out analogously to the synthesis of the compounds I starting from educts of the formulae IV and V.

The compounds of the formula I which are synthesized by the above-described processes can be subjected to further modifications on the

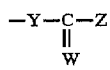

group by known methods, in particular in the event that Y is a direct bond, W is oxygen and Z is $OR^5$ (carboxylic ester).

a complex metal hydride or, in the case of an aldehyde or ketone, also hydrogen and a hydrogenation catalyst. To synthesize cyclohexanol derivatives, it is also possible to react suitable substituted phenols with hydrogen in the presence of a hydrogenation catalyst.

In the event that X is NH, the nucleophiles of the formula V which are required as starting materials can be prepared by known processes, for example by reducing an oxime or nitrile with a suitable reducing agent, for example a complex metal hydride or hydrogen in the presence of a hydrogena-

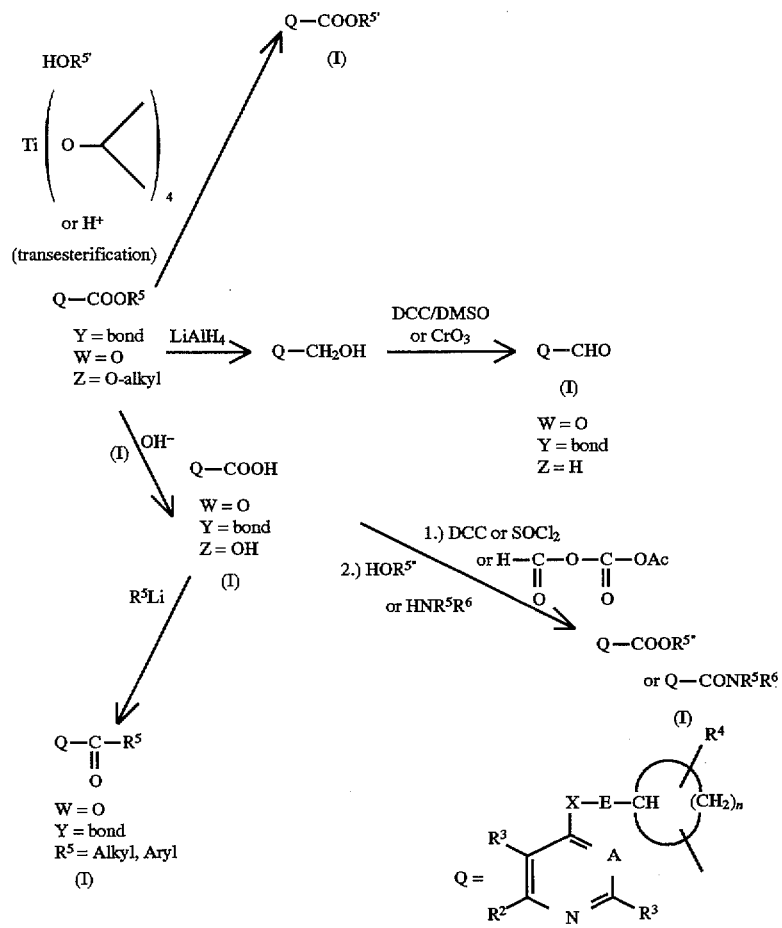

The reactions described are carried out analogously to known processes.

Transesterification: D. Seebach et al., Synthesis 1982, 138,
Alcohol oxidation: K. E. Pfitzner, J. G. Moffat, J. Amer. Chem. Soc. 87, 5661 (1965).
Conversion of carboxylic acids to ketones: M. J. Jorgenson, Org. Reactions 18, 1 (1970).

In the event that X is oxygen, the nucleophiles of the formula V which are required as starting materials can be prepared by known processes, for example by reducing a carbonyl group with a suitable reducing agent, for example tion catalyst, reductive amination or Leuckart-Wallach reaction of an aldehyde or ketone or Gabriel reaction of an alkyl halide or alkyl tosylate. To synthesize cyclohexylamine derivatives, it is also possible to react suitable substituted anilines with hydrogen in the presence of a hydrogenation catalyst.

Particularly suitable reactions for the preparation of the educts for the particularly preferred cyclohexyl derivatives are the following:

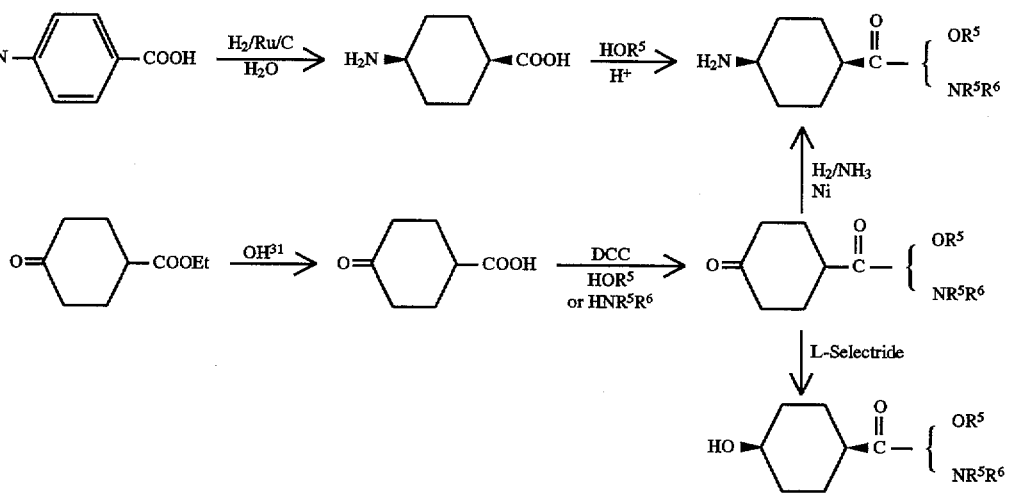

Preparation of the educts:

Methyl cis-4-aminocyclohexanecarboxylate L. H. Werner, S. Ricca, J. Amer. Chem. Soc. 80, 2733 (1958).
Ethyl cyclohexanone-4-carboxylate: H. Musso, K. Naumann, K. Grychtul, Chem. Ber. 100, 3614 (1967).

The active substances are suitable for controlling animal pests, in particular insects, arachnids, helminths and molluscs, very particularly preferably for controlling insects and arachnids, which are found in agriculture, in livestock breeding, in afforestations, in the protection of stored products and materials, and in the hygiene field, while being well tolerated by plants and having a favorable toxicity to warm-blooded species. They are active against normally sensitive and resistant species and against all or some stages of development. The abovementioned pests include:

From the order of the Acarina, for example, *Acarus siro*, Argas spp., Ornithodoros spp., *Dermanyssus gallinae*, *Eriophyes ribis*, *Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp..

From the order of the Isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and Scutigera spp..

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria*.

From the order of the Isoptera, for example, Reticulitermes spp.

From the order of the Anoplura, for example, *Phylloxera vastatrix*, Pemphigus spp., *Pediculus humanus corpotis*, Haematopinus spp. and Linognathus spp.

From the order of the Mallophaga, for example, Trichodecres spp. and Damalinea spp.

From the order of the Thysanoptera, for example, *Hercinothrips femoralis* and *Thrips tabaci*.

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella*, Homona magnanima and Tortfix viridana.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopsis* and Ceratophyllus spp.

From the order of the Arachnida, for example, *Scorpio maurus* and *Latrodectus mactans.*

From the class of the helminths, for example, Haemonchus, Trichostrongulus, Ostertagia, Cooperia, Chabertia, Strongyloides, Oesophagostomum, Hyostrongulus, Ancylostoma, Ascaris and Heterakis as well as Fasciola and plant-injurious nematodes, for example those of the genera Meloidogyne, Heterodera, Ditylenchus, Aphelenchoides, Radopholus, Globodera, Pratylenchus, Longidorus and Xiphinema.

From the class of the gastropods, for example, Deroceras spp., Arion spp., Lymnaea spp., Galba spp., Succinea spp., Biomphalaria spp., Bulinus spp., Oncomelania spp.

From the class of the Bivalves, for example, Dreissena spp.

The invention also relates to compositions, in particular insecticidal and acaricidal compositions, which comprise the compounds of the formula I in addition to suitable formulation auxiliaries.

The compositions according to the invention generally comprise 1 to 95% by weight of the active substances of the formula I.

They can be formulated in various ways, depending on the prevailing biological and/or chemicophysical parameters. The following are therefore suitable. possibilities for formulation:

Wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual formulation types are known in principle and are described, for example, in:

Winnacker-Küchler, "Chemische Technologie" [Chemical Technology], Volume 7, C. Hauser Verlag Munich, 4th Edition 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

The necessary formulation auxiliaries, such as inert materials, surfactants, solvents and other additives are also known and are described, for example, in:

Watkins, "Handbook of Insecticide Dust Diluents and Carriers", 2nd Ed., Darland Books, Caldwell N. J.; H. V. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface Active Ethylene Oxide Adducts], Wiss. Verlagsgesell., Stuttgart 1967; Winnacker-Küchler, "Chemische Technologie" [Chemical Technology], Volume 7, C. Hauser Verlag Munich, 4th Edition 1986.

Based on these formulations, it is also possible to prepare combinations with other pesticidally active substances, fertilizers and/or growth regulators, for example in the form of a readymix or a tank mix. Wettable powders are preparations which are uniformly dispersible in water and which, in addition to the active substance, also comprise wetting agents, for example polyethoxylated alkylphenols, polyethoxylated fatty alcohols, alkyl - and alkylphenolsulfonates, and dispersants, for example sodium lignosulfonate or sodium 2,2'-dinaphthylmethane-6,6'-disulfonate, in addition to a diluent or inert substance.

Emulsifiable concentrates are prepared by dissolving the active substance in an organic solvent, for example butanol, cyclohexanone, dimethylformamide, xylene or else higher-boiling aromatics or hydrocarbons, with the addition of one or more emulsifiers. Emulsifiers which can be used are, for example: calcium salts of alkylarylsulfonic acid, such as calcium dodecylbenzenesulfonate, or nonionic emulsifiers, such as fatty acid polyglycol esters, alkylaryl polyglycol ethers, fatty alcohol polyglycol ethers, propylene oxide/ ethylene oxide condensation products, alkyl polyethers, sorbitan fatty acid esters, polyoxyethylene sorbitan fatty acid esters or polyoxyyethylene sorbitol esters.

Dusts are obtained by grinding the active substance with finely divided solid substances, for example talc or natural clays, such as kaolin, bentonite or pyrophyllite or diatomaceous earth. Granules can be produced either by spraying the active substance onto adsorptive, granulated inert material or by applying active substance concentrates to the surface of carriers, such as sand, kaolinites or granulated inert material, by means of binders, for example polyvinyl alcohol, sodium polyacrylate or else mineral oils. Suitable active substances can also be granulated in the manner which is conventional for the production of fertilizer granules, if desired in a mixture with fertilizers.

The concentration of active substance in wettable powders is, for example, approximately 10 to 90% by weight, the remainder to 100% by weight is composed of conventional formulation components. In the case of emulsifiable concentrates, the concentration of active substance can be about 5 to 80% by weight. Formulations in the form of dusts usually comprise 5 to 20% by weight of active substance, sprayable solutions approximately 2 to 20% by weight. In the case of granules, the active substance content depends partly on whether the active ingredient is in liquid or solid form and on which granulation auxiliaries, fillers and the like are being used.

Besides, the abovementioned formulations of active substance comprise, if appropriate, the adhesives, wetting agents, dispersants, emulsifiers, penetrants, solvents, fillers or carriers which are conventional in each case.

For use, the concentrates, which are present in commercially available form, are diluted, if appropriate, in conventional manner for example using water in the case of wettable powders, emulsifiable concentrates, dispersions and in some cases of microgranules. Preparations in the form of dusts and granules as well as sprayable solutions are conventionally not further diluted with other inert substances prior to use.

The application rate required varies with the external conditions, such as, inter alia, temperature and humidity. It can vary within wide limits, for example between 0.0005 and 10.0 kg/ha or more of active substance, but it is preferably between 0.001 and 5 kg/ha.

The active substances according to the invention may be present in their commercially available formulations and in the use forms prepared from these formulations in the form of a mixture with other active substances, such as insecticides, attractants, sterilants, acaricides, nematicides, fungicides, growth-regulating substances or herbicides.

The pesticides include, for example, phosphoric esters, carbamates, carboxylic esters, formamidines, tin compounds, substances prepared by microorganisms and the like. Preferred components of the mixtures are 1. from the group of the phosphorus compounds acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachloroethyl phosphorthioate (SD 208 304), dimethoate, disulfoton, EPN, ethion, ethoprophos, etrimfos, famphur, fenamiphos, fenitrothion, fensulfothion, fenthion, fonofos, formothion, heptenophos, isazophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos, pirimiphos-ethyl, pirimiphosmethyl, profenofos, propaphos, proetamphos, prothiofos, pyraclofos, pyridaphenthion, quinalphos, sulprofos, temephos, terbufos, tetrachlorvinphos, thiometon, triazophos, trichlorphon, vamidothion;

2. from the group of the carbamates aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio (ethylideneamino) N-methyl-N-(morpholinothio) carbamate (UC 51717);

3. from the group of the carboxylic esters allethrin, alphametrin, 5-benzyl-3-furylmethyl (E)-(1R) cis-2,2-dimethyl-3-(2-oxothiolan-3-ylidenemethyl) cyclopropanecarboxylate, bioallethrin, bioallethrin ((S)-cyclopentyl isomer), bioresmethrin, biphenate, (RS)-1-cyano-1-(6-phenoxy-2-pyridyl)methyl-(1RS)-trans-3 - ( 4 - t e r t - b u t y l p h e n y l ) - 2 , 2 -dimethylcyclopropanecarboxylate (NCI 85193), cycloprothrin, cyhalothrin, cythithrin, cypermethrin, cyphenothrin, deltamethrin, empenthrin, esfenvalerate, fenfluthrin, fenpropathrin, fenvalerate, flucythrinate, flumethrin, fluvalinate (D isomer), permethrin, phenothrin ((R) isomer), d-pralethrin, pyrethrins (natural products), resmethrin, tefluthrin, tetramethrin, tralomethrin;

4. from the group of the amidines amitraz, chlordimeform;

5. from the group of the tin compounds cyhexatin, fenbutatin oxide;

6. others abamectin, *Bacillus thuringiensis*, bensultap, binapacryl, bromopropylate, buprofezin, camphechlor, cartap, chlorobenzilate, chlorfluazuron, 2-(4-chlorophenyl)-4,5-diphenylthiophene (UBI-T 930), clofentezine, 2-naphthylmethyl cyclopropanecarboxylate (Ro 12-0470), cyromazin, ethyl N-(3,5-dichloro-4-(1,1,2,3,3,3-hexafluoro-1-propyloxy)phenyl) carbamoyl)-2-chlorobenzocarboximidate, DDT, dicofol, N-(N-(3,5-dichloro-4-(1,1,2,2-tetrafluoroethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl) propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl) diphenyl ether (MTI 800), granulosis and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (DS 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam, trifumuron, imidacloprid.

The active substance content of the use forms prepared from the commercially available formulations can be from 0.00000001 up to 95% by weight of active substance, and is preferably between 0.00001 and 1% by weight.

Application is effected in a conventional manner, matched to the use forms.

The active substances according to the invention are also suitable for controlling endoparasites and ectoparasites in the field of veterinary medicine and in the field of animal keeping.

In this sector, the active substances according to the invention are applied in the known manner, such as oral administration in the form of, for example, tablets, capsules, drinks, granules, by dermal administration in the form of, for example, dipping, spraying, pouring-on and spotting-on and dusting, as well as by parenteral administration in the form of, for example, an injection.

Accordingly, the novel compounds of the formula I according to the invention can also be employed particularly advantageously in livestock production (for example cattle, sheep, pigs and poultry, such as chickens, geese and the like). In a preferred embodiment of the invention, the novel compounds, if appropriate in the form of suitable formulations (cf. above) and, if appropriate, together with the drinking water or feed, are administered orally to the animals. Since they are effectively excreted with the feces, it is very simple to prevent the development of insects in the feces of the animals in this way. The doses and formulations which are suitable in each case depend, in particular, on the species and the development stage of the productive animals and also on the intensity of infestation and can be readily identified and determined by customary methods. In the case of cattle, for example, the novel compounds can be employed at doses from 0.01 to 1 mg/kg of body weight.

The compounds of the formula I according to the invention are also distinguished by an outstanding fungicidal activity. Fungal pathogens which have already penetrated the plant tissue can successfully be controlled curatively.

23

This is particularly important and advantageous in the case of those fungal diseases which can no longer be controlled effectively with the conventional fungicides once infection has taken place. The spectrum of action of the claimed compounds embraces a variety of economically important phytopathogenic fungi such as, for example, *Plasmopara viticola, Erysiphe graminis* and *Puccinia recondita.*

Besides, the compounds according to the invention are also suitable for use in industrial areas, for example as a wood preservative, as a preservative in paints, in cooling lubricants for metalworking, or as a preservative in drilling and cutting oils.

The active substances according to the invention can be used in their commercially available formulations either alone or in combination with other fungicides known from the literature.

Examples of fungicides which are known from the literature and which can be combined according to the invention with the compounds of the formula I are the following products:

aldimorph, andoprim, anilazine, BAS 480F, BAS 450F, benalaxyl, benodanil, benomyl, binapacryl, bitertanol, bromuconazole, buthiobate, captafol, captan, carbendazim, carboxin, CGA 173506, cyprofuram, dichlofluanid, diclomezine, diclobutrazole, diethofencarb, difenconazole (CGA 169374), difluconazole, dimethirimol, dimethomoph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF 164), fluazinam, fluobenzimine, fluquinconazole, fluorimide, flusilazole, flutolanil, flutriafol, folpet, fosetyl-aluminum, fuberidazole, fulsulfamide (MT-F 651), furalaxyl, furconazole, furmecyclox, guazatine, hexaconazole, ICI A5504, imazalil, imibenconazole, iprobenfos, iprodione, isoprothiolane, KNF 317, copper compounds, such as copper oxychloride, oxine-copper, copper oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidon, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiophanate-methyl, thiram, tolclofos-methyl, tolylfluanid, triadimefon, triadimenol, tricyclazole, tridemorph, triflumizol, triforine, validamycin, vinchlozolin, XRD 563, zineb, sodium dodecylsulfonate, sodium dodecyl sulfate, sodium C13/C15-alcohol ether sulfonate, sodium cetostearyl phosphate ester, dioctyl sodium sulfosuccinate, sodium isopropyl naphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternized fatty amines, alkyldimethylbenzylammonium chloride and 1-hydroxyethyl-2-alkylimidazoline.

The abovementioned components are known active substances, many of which are described in Ch. R Worthing, S. B. Walker, The Pesticide Manual, 7th Edition (1983), British Crop Protection Council. The active substance content of the use forms prepared from the commercially available formulations can be varied within wide limits, the concentration of active substance of the use forms can be from 0.0001 to 95% by weight of active substance and is preferably between 0.0001 and 1% by weight. They are applied in a customary manner adapted to suit the use forms.

The examples which follow are intended to illustrate the invention

I. FORMULATION EXAMPLES a) A dust is obtained by mixing 10 parts by weight of active substance and 90 parts by weight of talc as inert substance and comminuting the mixture in a hammer mill.

b) A wettable powder which is readily dispersible in water is obtained by mixing 25 parts by weight of active substance, 65 parts by weight of kaolin-containing quartz as inert substance, 10 parts by weight of potassium lignosulfonate and 1 part by weight of sodium oleoylmethyltaurinate as wetting agent and dispersant and grinding the mixture in a pinned disk mill.

c) A dispersion concentrate which is readily dispersible in water is prepared by mixing 40 parts by weight of active substance with 7 parts by weight of a sulfosuccinic monoester, 2 parts by weight of a sodium lignosulfonate and 51 parts by weight of water and grinding the mixture in a ball mill to a fineness of below 5 microns.

d) An emulsifiable concentrate can be prepared from 15 parts by weight of active substance, 75 parts by weight of cyclohexane as the solvent and 10 parts by weight of ethoxylated nonylphenol (10 EO) as emulsifier.

e) Granules can be prepared from 2 to 15 parts by weight of active substance and an inert carrier material for granules, such as attapulgite, pumice granules and/or quartz sand. It is expedient to use a suspension of the wettable powder of Example b) with a solids content of 30%, and to spray this suspension onto the surface of attapulgite granules and to dry and mix these intimately. The wettable powder thus amounts to approximately 5% by weight and the inert carrier material to approximately 95% by weight of the finished granules.

II. BIOLOGICAL EXAMPLES

Fungicidal Activity

Example 1

*Plasmopara viticola*

Approximately 6 weeks after sowing, grapevine seedlings cvs. "Riesling/Ehrenfelder" were treated until dripping wet with aqueous suspensions of the claimed compounds. After the spray coating had dried on, the plants were inoculated with a zoosporangia suspension of *Plasmopara viticola* and, while dripping wet, placed for 4 to 5 hours in a controlled-environment cabinet at 23° C. and a relative atmospheric humidity of 80 to 90%.

After an incubation time of 7 days in the greenhouse, the plants were returned overnight to the controlled-environment cabinet so as to stimulate sporulation of the fungus. The disease level was subsequently evaluated. It was expressed in % diseased leaf area in comparison with the untreated, 100% diseased control plants.

At 250 mg of active substance/l of spray mixture, the following substances suppress the disease completely: Example Nos. 82, 83.

Example 2

*Puccinia recondita*

Wheat cv. "Jubilar" in the 2-leaf stage was treated with aqueous suspensions of the claimed compounds until dripping wet.

After the spray coating had dried on, the plants were inoculated with an aqueous spore suspension of *Puccinia recondita*. The dripping wet plants were placed for approximately 16 hours in a controlled-environment cabinet at 20° C. and a relative atmospheric humidity of approximately 100%. They were subsequently grown on in a greenhouse at a temperature of 22° to 25° C. and a relative atmospheric humidity of 50 to 70%.

After an incubation time of approximately 2 weeks, the fungus sporulated on the entire leaf surface of the untreated control plants (100% disease), so that the disease level of the test plants could be evaluated. The disease level was expressed in % of diseased leaf area in comparison with the untreated, 100% diseased control plants.

At 250 mg/l of spray mixture, the following substance suppressed the disease completely: Example No. 82.

Example 3

*Erysiphe graminis*

Barley plants in the 3-leaf stage were densely inoculated with conidia of powdery mildew of barley (*Erysiphe graminis f.* sp. hordei) and placed in a greenhouse at 20° C. and a relative atmospheric humidity of 90 to 95%. 24 hours after inoculation, the plants were wetted uniformly with the compounds listed in Table 1 at the concentrations of active substance indicated. After an incubation time of 10 days, the plants were examined for disease with powdery mildew of barley. The disease level was expressed in % of diseased leaf area based on untreated, 100% diseased control plants.

At 250 mg of active substance/l of spray mixture, the following substances suppressed the disease completely; Example Nos. 82, 83, 68.

Insecticidal Activity

Example 4:

Young rice plants (*Oryza sativa*) were immersed in aqueous dilutions of a wettable powder concentrate at a concentration of 250 ppm (based on active substance) and, after the treatment mixture had run off, populated with L4-larvae of the brown planthopper *Nilaparvata lugens*. After the test animals had been introduced into a test cage, they were observed for 3 days at 28° C. and high atmospheric humidity and their mortality was determined.

At 250 ppm, the compounds of Examples 70 and 82 resulted in a 100% mortality of the test animals.

Example 5

Larvae (L3) of the Southern Corn Rootworm (*Diabrotica undecimpunctata*) were placed on filter paper disks which had been soaked in 1 ml of a dilution of a wettable powder in acetone at a concentration of 250 ppm based on active substance. After the acetone had been evaporated, the dishes were sealed and stored for 3 days at 28° C., and the mortality of the larvae was determined thereafter.

The compounds of Examples 68, 70, 82, 98 and 207 showed a mortality of 100%.

Example 6

Petri dishes half filled with a synthetic feed diet were populated with L3 larvae of the Egyptian cotton leafworm *Spodoptera littoralis*, and the larvae were sprayed with an aqueous suspension of a wettable powder concentrate comprising 250 ppm of active substance. The dishes were sealed, and, after 5 days, the larvae were examined for mortality.

The compounds of Examples 70 and 82 showed a destruction of 100%.

Example 7

The inside of bottom and lid of glass Petri dishes were coated with in each case 3 ml of a solution of the wettable powder concentrate in acetone, active compound content 250 ppm, and then placed into a fume cabinet for 1 hour to allow the acetone to evaporate. The dishes were then populated with adult houseflies (*Musca domestica*) and sealed, and the mortality of the flies was determined after 3 hours.

A destruction of 100% was achieved with the compounds of Examples 66, 68, 70, 96, 98, 207 and 224.

Example 8

Field beans (*Vicia faba*) densely populated with cowpea aphid (*Aphis craccivora*) were sprayed with aqueous dilutions of wettable powder concentrates comprising 250 ppm of active substance until they reached the stage of the start of run off. After 3 days, the mortality of the aphids was determined.

A destruction of 100% was achieved with the compounds of Examples 68, 82 and 83.

Example 9

Bean plants (Phaseolus v.) severely infested with greenhouse red spider mites (*Tetranychus urticae*, complete population) were sprayed with the aqueous dilution of an emulsion concentrate comprising 250 ppm of the active substance in question. After 7 days, the mortality of the mites was checked. A 100% destruction was achieved using the compounds of Examples 82, 83 and 96.

Example 10

Bean plants densely populated with whitefly (*Trialeurodes vaporariorum*) were sprayed with aqueous suspensions of wettable powder concentrates (active substance content 250 ppm) until they had reached the stage of the start of run off. After the plants had been placed in a greenhouse, they were checked microscopically after 14 days, resulting in a mortality of 100% in the case of each of the preparations of active substances of the tabulated Examples 68 and 82.

Example 11

Larvae (L4) of the cockroach *Blaberus craniifer* were injected with active substances dissolved in methanol. A mortality of 100% was found 48 hours after application of the compounds of Examples 66, 70, 207 and 224 ($2\times10^{-4}$ g of a.i./animal).

Example 12

Larvae (L4) of the tobacco hornworm *Manduca sexta* were injected with active substances dissolved in acetone.

A mortality of 100% was found 48 hours after application of the compounds of Examples 70 and 207 ($2\times10^{-4}$ g of a.i./animal).

Use as an Antiparasitic

Example 1

In vitro test on tropical cattle ticks (*Boophilus microplus*)

The following experimental setup demonstrated the activity of the compounds according to the invention against ticks:

To prepare a suitable preparation of active substance, the active substances were dissolved in a mixture composed of dimethylformamide (85 g), nonylphenol polyglycol ether (3 g) an ethoxylated castor oil (7 g) to give a 10% (w/v) solution, and the resulting emulsion concentrate was diluted with water to a test concentration of 500 ppm.

Batches of ten satiated females of the tropical tick, *Boophilus microplus*, were immersed for five minutes in these dilutions of active substance. The ticks were subsequently dried on filter paper, and their backs were then attached to an adhesive film for oviposition purposes. The ticks were kept in an incubation cabinet at 28° C. and at atmospheric humidity of 90%.

As a control, female ticks were immersed in plain water. The inhibition of oviposition was used two weeks after the treatment to assess the activity. 100% means that no tick had deposited eggs and 0 that all had deposited eggs.

In this test, the compounds of Examples 70 and 82 caused in each case a 100% inhibition of oviposition at an active substance concentration of 500 ppm.

III. PREPARATION EXAMPLES

Example A 4-(cis-4-Methoxycarbonylcyclohexylamino)-5-chloro-6-ethylpyrimidine

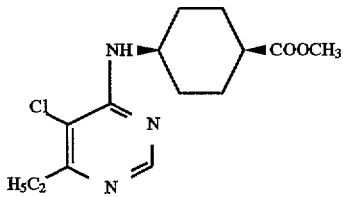

42.5 g (0.24 mol) of 4,5-dichloro-6-ethylpyrimidine, 37.5 g (0.24 mol) of methyl cis-4-aminocyclohexanecarboxylate and 36.4 g (0.36 mol) of triethylamine are heated for 6 hours at 80°, without solvent. After the mixture has cooled to room temperature it is taken up in water/methylene chloride, and the organic phase is dried and concentrated on a rotary evaporator. This gives 69 g of a brown oil (96.5% of theory) which can be reacted further without further purification.

For further purification, the product can be chromatographed on silica gel using petroleum ether/ethyl acetate 2:1. This gives a yellow oil which crystallizes upon standing.

M.p. 81°–82° C.

Example B

5-Chloro-6-ethyl-4-(cis-4-isopropoxycarbonylcyclohexylamino)pyrimidine

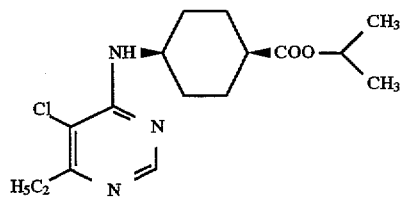

1.5 g (5.0 mmol) of the methyl ester of Example A and 500 mg of titanium(IV) isopropylate are refluxed for 4 hours in 50 ml of isopropanol. The isopropanol is stripped off, and the residue is taken up in water/methylene chloride. After chromatography on silica gel using petroleum ether/ethyl acetate 1:1, there remain 1.1 g of a colorless oil (67.5% of theory) which crystallizes upon standing (m.p. 85°–86° C.).

Example C 4-(cis-4-tert-Butoxycarbonylcyclohexylamino)-5-chloro-6-ethylpyrimidine

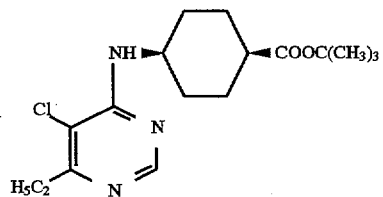

3.5 g (0.02 mol) of 4,5-dichloro-6-ethylpyrimidine, 4.0 g of tert-butyl 4-aminocyclohexanecarboxylate (0.02 mol) and 3.0 g of triethylamine (0.03 mol) are heated for 6 hours at 90°, without solvent. After the mixture has cooled to room temperature, it is taken up in water/methylene chloride, and the organic phase is dried and concentrated. For purification and separation of the cis/trans isomers, the product is chromatographed on silica gel using petroleum ether/ethyl acetate 7:3. First, 1.0 g of a colorless oil (trans isomer) and, after a mixed fraction (1.0 g), 2.8 g of cis isomer are obtained as a colorless oil which crystallizes upon standing. M.p.: 87°–88° C.

| NMR data: | |
|---|---|
| trans isomer (CDCl$_3$) | 5.08 d NH |
|  | 4.00 m (broad) NH—CH |
| cis isomer (CDCl$_3$) | 5.19 d NH |
|  | 4.08 m (narrow) NH—CH |

Preparation of the Precursors tert-Butyl 4-aminocyclohexanecarboxylate

In an autoclave, 10.3 g (52 mmol) of tert-butyl 4-cyclohexanonecarboxylate are hydrogenated at 100° C. and 100 bar in 200 ml of ammonia-saturated methanol in the presence of 5 g of Raney nickel. After the catalyst has been removed by filtration, the product is concentrated and the oily residue purified by distillation on a thin-film evaporator (140°/0.5 mm). This gave 5.7 g (55.1% of theory) of a colorless oil (cis/trans isomer mixture).

tert-Butyl 4-cyclohexanecarboxylate

A solution of 48.2 g of dicyclohexylcarbodiimide in 100 ml of methylene chloride is added dropwise at room temperature with stirring to a solution of 27.7 g (0.2 mol) of 4-cyclohexanecarboxylic acid, 28.9 g of tert-butanol and 24 g of 4-dimethylaminopyrimidine in 200 ml of methylene chloride. The mixture is stirred for 24 hours at room temperature, dicyclohexylurea is removed by filtration, and the product is extracted twice by stirring with water. The organic phase is dried and concentrated. The crude product is purified by distillation on a thin-film evaporator (150°/0.4 mm). This gives 20 g (51.8% of theory) of a colorless oil.
4-Cyclohexanonecarboxylic acid 33.5 g (0.21 mol) of methyl 4-cyclohexanonecarboxylate (Chem. Bet. 100, 3614 (1967)) are stirred in 125 ml of 8% sodium hydroxide solution until a clear solution has formed. The mixture is extracted once by stirring with toluene, and the aqueous phase is acidified with concentrated hydrochloric acid. Since the carboxylic acid did not precipitate, the water was stripped off on a rotary evaporator and the solid residue extracted repeatedly using methylene chloride. This gave 27.7 g (92.9% of theory) of a colorless solid which was reacted further without further purification.

Example D cis-4-(5-Chloro-6-ethylpyrimidin-4-ylamino)cyclohexanecarboxylic acid

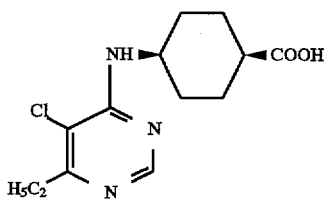

6.0 g (0.02 mol) of the ester of Example A are added to a solution of 1.6 g (0.04 mol) of caustic soda in 50 ml of methanol and the solution is stirred for 8 hours at 50° C. The pH is brought to 2 by adding concentrated hydrochloric acid. After the solvent has been stripped off, the solid residue is extracted repeatedly using methylene chloride/methanol 1:1 and the organic phase is concentrated. 5.1 g (50% of theory) of a colorless solid remain. M.p.: >255° decomposition (hydrochloride).

Example E

5-Chloro-6-ethyl-4-[cis-4-(2-phenyl-2-propoxycarbonyl)cyclohexylamino]pyrimidine

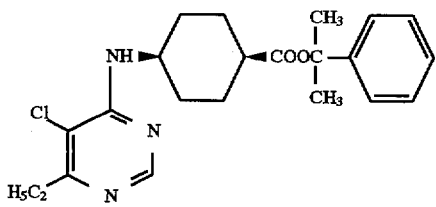

0.7 g (2.5 mmol) of the carboxylic acid of Example D is stirred with 2 ml of thionyl chloride and 1 drop of dimethylformamide until the evolution of gas has ceased. 50 ml of toluene are added, and the solvent is stripped off on a rotary evaporator. This is repeated once. There remains a colorless solid (hydrochloride of the carboxylic acid chloride), which is introduced into a solution of 680 mg of 2-phenyl-2-propanol and 250 mg of 4-dimethylaminopyridine in 5 ml of pyridine. The mixture is heated for 2 hours at 60°, cooled to room temperature and then diluted with 25 ml of water. The mixture is rendered weakly acidic by adding concentrated hydrochloric acid and subsequently extracted by stirring twice with methylene chloride. The combined organic phases are dried and concentrated. After chromatography of the crude product on silica gel using petroleum ether/ethyl acetate 7:3, 150 mg (14.9% of theory) of a colorless oil remain.

Example F

5-Chloro-6-ethyl-4-[cis-4-(1,2,3,4-tetrahydroisoquinolin-2-ylcarbonyl)cyclohexylamino]pyrimidine

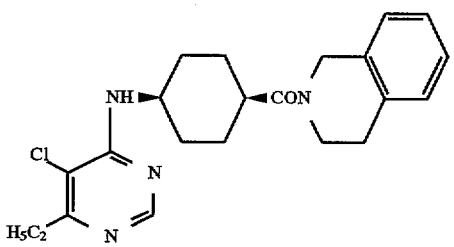

Using 700 mg (2.5 mmol) of the carboxylic acid of Example D, the hydrochloride of the carboxylic acid chloride is prepared analogously to Example E. This product is introduced into a solution of 350 mg of 1,2,3,4-tetrahydroisoquinoline and 500 mg of triethylamine in 25 ml of methylene chloride. The batch is stirred for 4 hours at room temperature and extracted by stirring with water, and the organic phase is separated off, dried and concentrated. This gives 0.7 g (70.2% of theory) of a yellow oil which crystallizes upon standing. M.p.: 98°–99° C.

Example G

5-Chloro-6-ethyl-4-(cis-4-pivaloyloxycyclohexyloxy)pyrimidine

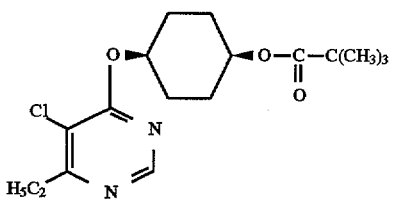

0.5 ml (4.2 mmol) of pivaloyl chloride are added dropwise with cooling to a solution of 0.85 g (3.3 mmol) of 5-chloro-6-ethyl-4-(cis-4-hydroxycyclohexyloxy)pyrimidin in 10 ml of pyrimidine, and the mixture is stirred at room temperature until the reaction is complete (approximately 1 hour). The reaction mixture is concentrated to dryness in vacuo, the product is taken up in ether and the mixture is washed with dilute ammonium chloride solution. The organic phase is dried over magnesium sulfate and concentrated in vacuo. The residue is purified by flash chromatography (silica gel, petroleum ether/ethyl acetate=6:4). 0.6 g (53%) of product is obtained as colorless crystals (m.p.: 62° C.).

Preparation of Precursors

5-Chloro-6-ethyl-4-(cis-4-hydroxycyclohexyloxy)pyrimidine

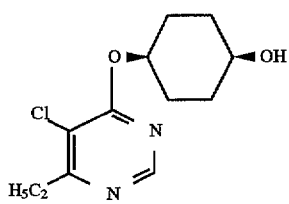

410 mg (10.8 mmol) of sodium borohydride are added at 0° C. to a solution of 10 g (39.2 mmol) of 4-(5-chloro-6-ethylpyrimidin-4-yloxy)cyclohexanone in 200 ml of ethanol and the mixture is stirred until the reaction is complete (approximately 6 hours). The reaction solution is concentrated in vacuo, the residue is taken up in 200 ml of ether and the mixture is washed thoroughly using water. The organic phase is dried over magnesium sulfate and concentrated in vacuo. The residue is purified by flash chromatography (silica gel, petroleum ether/ethyl acetate=6:4). This gives 3.5 g (35%) of the cis isomer (higher $R_f$ value) and 2.0 g (20%) of the trans isomer.

4-(5-Chloro-6-ethylpyrimidin-4-yloxy)cyclohexanone

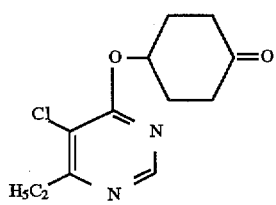

19 g (64 mmol) of 5-chloro-6-ethyl-(1,4-dioxaspiro[4,5]dec-8-yloxy)pyrimidine are suspended with vigorous stirring at room temperature for 24 hours in a mixture of 220 ml of THF and 120 ml of 2N HCl. After 100 ml of diethyl ether have been added, the aqueous phase is separated off, and the organic phase is subsequently neutralized using sodium hydrogencarbonate. Again, the aqueous phase is removed, and the organic phase is dried over magnesium sulfate and concentrated in vacuo. The residue is purified by flash chromatography (silica gel, petroleum ether/ethyl acetate= 6:4). This gives 11.2 g (69%) of a yellowish oil.

5-Chloro-6-ethyl-4-(1,4-dioxaspiro[4,5]dec-8-yloxy)pyrimidine

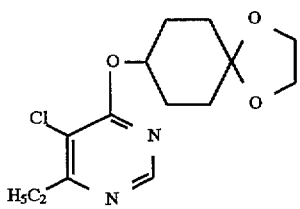

5 g (0.16 mol) of 80% sodium hydride are added to a solution of 19 g (0.12 mol) of 4-hydroxycyclohexanone ethylene acetal in 200 ml of absolute THF and the mixture is refluxed for 1 hour. The reaction solution is then cooled to room temperature and 21.2 g (0.12 mol) of 4,5-dichloro-6-ethylpyrimidine are added dropwise. The reaction mixture is refluxed for a further 2 hours. To destroy excess sodium hydride, 20 ml of isopropanol are slowly added dropwise, and the reaction mixture, which is still warm, is stirred for a further 30 minutes. 100 ml of aqueous ammonium chloride solution are subsequently added, the aqueous phase is extracted using ether, and the combined organic phases are dried over magnesium sulfate. The solvent is concentrated in vacuo to dryness. This gives 35.0 g (93%) of a yellow oil. The crude product can be reacted further without further purification.

4-Hydroxycyclohexanone ethylene ketal

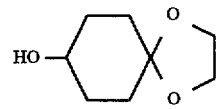

3.6 g (0.095 mol) of sodium borohydride are added to a solution of 50 g (0.252 mol) of cyclohexanedione monoethylene ketal in 300 ml of ethanol and the mixture is stirred for approximately 2 hours until the reaction is complete. To destroy excess sodium borohydride, 30 ml of acetone are added dropwise and the mixture is stirred for a further 10 minutes. Then, 50 ml of $H_2O$ are added with vigorous stirring and the mixture is stirred for a further 15 minutes. The reaction mixture is subsequently concentrated on a rotary evaporator and the residue is taken up in diethyl ether. The organic phase is washed with water, dried over $MgSO_4$ and concentrated. Thorough drying gives 46 g (91%) of a yellowish oil. The resulting crude product can be reacted further without further purification.

Example H 4-(cis-4-Benzoyloxycyclohexyloxy)-5-chloro-6-ethylpyrimidine

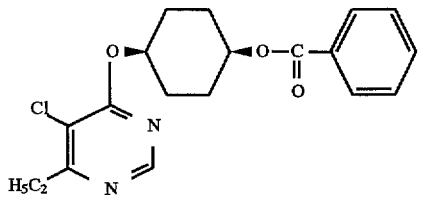

Prepared analogously to Example G starting from 1.0 g (3.9 mmol) of 5-chloro-6-ethyl-4-(cis-4-hydroxycyclohexyloxy)pyrimidine and 0.6 g (4.3 mmol) of benzoyl chloride. 0.93 g (63% of theory) of colorless crystals are obtained. M.p.: 69°–71° C.

Example I 4-(4-Acetylcyclohexylamino)-5-chloro-6-ethylpyrimidine

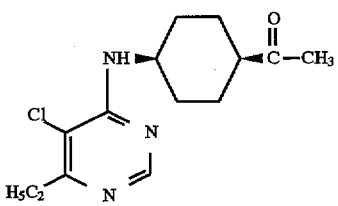

25 ml of a 5% solution of methyllithium in diethyl ether are added dropwise at –10°–0° C. to a suspension of 3.7 g of the carboxylic acid of Example D in 75 ml of tetrahydrofuran. A voluminous colorless precipitate is formed. Stirring is continued for 3 hours at room temperature, the mixture is poured onto ice, toluene is added, and the organic phase is separated off. After drying and concentration, the crude product is chromatographed on silica gel using ethyl acetate. First, the trans isomer (150 mg, m.p.: 99°–100° C.)

is eluted, followed by the cis isomer (200 mg, m.p.: 78°–79° C.).

TABLE 1

| Ex. No. | R² | R³ | X | Y | Configuration on the cyclohexane | Z | M.p. [°C.] |
|---|---|---|---|---|---|---|---|
| 1 | C₂H₅ | Cl | NH | — | cis | H | |
| 2 | " | Br | " | — | " | H | |
| 3 | i-C₃H₇ | Cl | " | — | " | H | |
| 4 | CH₂OCH₃ | OCH₃ | " | — | " | H | |
| 5 | " | Cl | " | — | " | H | |
| 6 | CF₃ | OCH₃ | " | — | " | H | |
| 7 | C₂H₅ | F | " | — | " | CH₃ | |
| 8 | " | Cl | " | — | " | " | 78–79 |
| 9 | " | Br | " | — | " | " | |
| 10 | i-C₃H₇ | Cl | " | — | " | " | |
| 11 | " | Br | " | — | " | " | |
| 12 | CH₂OCH₃ | OCH₃ | " | — | " | " | |
| 13 | " | Cl | " | — | " | " | |
| 14 | CF₃ | OCH₃ | " | — | " | " | |
| 15 | C₂H₅ | F | " | — | " | C₂H₅ | |
| 16 | — | Cl | " | — | " | " | |
| 17 | " | Br | " | — | " | " | |
| 18 | CH₂OCH₃ | OCH₃ | " | — | " | " | |
| 19 | C₂H₅ | F | NH | — | cis | n-C₃H₇ | |
| 20 | " | Cl | " | — | " | " | |
| 21 | " | Br | " | — | " | " | |
| 22 | CH₂OCH₂ | OCH₃ | NH | — | cis | n-C₃H₇ | |
| 23 | C₂H₅ | F | " | — | " | i-C₃H₇ | |
| 24 | " | Cl | " | — | " | " | |
| 25 | " | Br | " | — | " | " | |
| 26 | CH₂OCH₃ | OCH₃ | " | — | " | i-C₃H₇ | |
| 27 | C₂H₅ | Cl | " | — | " | n-C₄H₉ | |
| 28 | CH₂OCH₃ | OCH₃ | " | — | " | " | |
| 29 | C₂H₅ | Cl | " | — | " | —CH₂—CH(CH₃)₂ | |
| 30 | CH₂OCH₃ | OCH₃ | " | — | " | " | |
| 31 | C₂H₅ | Cl | " | — | " | CHCH₃C₂H₅ | |
| 32 | " | Br | " | — | " | " | |
| 33 | CH₂OCH₃ | OCH₃ | " | — | " | " | |
| 34 | CH₃ | Cl | " | — | " | t-C₄H₉ | |
| 35 | C₂H₅ | F | " | — | " | " | |
| 36 | " | Cl | " | — | " | " | |
| 37 | " | Br | " | — | " | " | |
| 38 | " | I | " | — | " | " | |
| 39 | Cyclopropyl | Cl | " | — | " | " | |
| 40 | n-C₃H₇ | " | " | — | " | " | |
| 41 | i-C₃H₇ | " | " | — | " | " | |
| 42 | i-C₃H₇ | Br | NH | — | cis | t-C₄H₉ | |
| 43 | CH₂OCH₃ | OCH₃ | " | — | " | " | |
| 44 | " | Cl | " | — | " | " | |
| 45 | CF₃ | OCH₃ | " | — | " | " | |
| 46 | C₂H₅ | CN | " | — | " | " | |
| 47 | C₂H₅ | Cl | " | — | " | -nC₈H₁₇ | |
| 48 | C₂H₅ | Cl | NH | " | cis | Phenyl | |
| 49 | " | Br | " | — | " | " | |
| 50 | " | CN | " | — | " | " | |
| 51 | CH₂OCH₃ | OCH₃ | NH | — | " | " | |
| 52 | " | Cl | " | — | " | " | |
| 53 | n-C₃H₇ | " | " | — | " | " | |
| 54 | i-C₃H₇ | " | " | — | " | " | |
| 55 | " | Br | " | — | " | " | |
| 56 | CF₃ | OCH₃ | " | — | " | " | |
| 57 | CH₃ | Cl | " | — | " | 2-Thienyl | |
| 58 | C₂H₅ | " | " | — | " | " | |
| 59 | " | Br | " | — | " | " | |
| 60 | i-C₃H₇ | Cl | " | — | " | " | |
| 61 | CH₂OCH₃ | OCH₃ | " | — | " | " | |
| 62 | " | Cl | " | — | " | " | |
| 63 | CF₃ | OCH₃ | " | — | " | " | |

TABLE 1-continued

| Ex. No. | R² | R³ | X | Y | Configuration on the cyclohexane | Z | M.p. [°C.] |
|---|---|---|---|---|---|---|---|
| 64 | C₂H₅ | Cl | " | — | " | OCH₃ | 81–82 |
| 65 | CH₂OCH₃ | OCH₃ | NH | — | cis | OCH₃ | |
| 66 | C₂H₅ | Cl | " | — | " | OC₂H₅ | 79–80 |
| 67 | CH₂OCH₃ | OCH₃ | " | — | " | " | |
| 68 | C₂H₅ | Cl | " | — | " | O-nC₃H₇ | Oil |
| 69 | CH₂OCH₃ | OCH₃ | " | — | " | " | |
| 70 | C₂H₅ | Cl | " | — | " | O-iC₃H₇ | 85–86 |
| 71 | " | Br | " | — | " | " | |
| 72 | i-C₃H₇ | Cl | " | — | " | " | |
| 73 | CH₂OCH₃ | OCH₃ | " | — | " | " | |
| 74 | CH₂OCH₃ | Cl | NH | — | cis | O-iC₃H₇ | |
| 75 | CF₃ | OCH₃ | " | — | " | " | |
| 76 | C₂H₅ | Cl | " | — | " | O(CH₂)₃CH₃ | |
| 77 | " | " | " | — | " | OCHCH₃C₂H₅ | |
| 78 | CH₂OCH₃ | OCH₃ | " | — | " | " | |
| 79 | C₂H₅ | Cl | " | — | " | OCH₂CH(CH₃)₂ | |
| 80 | CH₃ | Cl | " | — | " | OC(CH₃)₃ | |
| 81 | C₂H₅ | F | " | — | " | " | |
| 82 | " | Cl | " | — | " | " | 87–88 |
| 83 | " | " | " | — | trans | " | Oil |
| 84 | " | Br | " | — | cis | " | |
| 85 | " | I | " | — | " | " | |
| 86 | " | CN | " | — | " | " | |
| 87 | i-C₃H₇ | Cl | " | — | " | " | |
| 88 | i-C₃H₇ | Br | NH | — | cis | OC(CH₃)₃ | |
| 89 | Cyclopropyl | Cl | " | — | " | " | |
| 90 | CH₂OCH₃ | OCH₃ | " | — | " | " | |
| 91 | " | Cl | " | — | " | " | |
| 92 | CF₃ | OCH₃ | " | — | " | " | |
| 93 | C₂H₅ | Cl | " | — | " | OC(CH₃)₂C₂H₅ | |
| 94 | CH₂OCH₃ | OCH₃ | " | — | " | " | |
| 95 | C₂H₅ | Cl | " | — | " | O(CH₂)₅CH₃ | |
| 96 | " | " | " | — | " | OCH(CH₃)(CH₂)₄CH₃ | Oil |
| 97 | CH₂OCH₃ | OCH₃ | " | — | " | " | |
| 98 | C₂H₅ | Cl | " | — | " | O(CH₂)₇CH₃ | Oil |
| 99 | CH₂OCH₃ | OCH₃ | " | — | " | " | |
| 100 | C₂H₅ | Cl | NH | — | cis | OCH₂C₆H₅ | |
| 101 | CH₂OCH₃ | OCH₃ | " | — | " | " | |
| 102 | C₂H₅ | Cl | " | — | " | OCHCH₃C₆H₅ | Oil |
| 103 | CH₂OCH₃ | OCH₃ | " | — | " | " | |
| 104 | C₂H₅ | Cl | " | — | " | OC(CH₃)₂C₆H₅ | Oil |
| 105 | CH₂OCH₃ | OCH₃ | " | — | " | " | |
| 106 | C₂H₅ | Cl | " | — | " | Cyclopropyloxy | |
| 107 | CH₂OCH₃ | OCH₃ | " | — | " | " | |
| 108 | C₂H₅ | Cl | " | — | " | Cyclobutyloxy | |
| 109 | CH₂OCH₃ | OCH₃ | " | — | " | " | |
| 110 | C₂H₅ | Cl | " | — | " | Cyclopentyloxy | |
| 111 | CH₂OCH₃ | OCH₃ | NH | — | cis | Cyclopentyloxy | |
| 112 | C₂H₅ | Cl | " | — | " | Cyclohexyloxy | |
| 113 | CH₂OCH₃ | OCH₃ | " | — | " | " | |
| 114 | C₂H₅ | Cl | " | — | " | Cycloheptyloxy | |
| 115 | CH₂OCH₃ | OCH₃ | " | — | " | " | |
| 116 | C₂H₅ | Cl | " | — | " | cis-4-Methylcyclohexyloxy | |
| 117 | CH₂OCH₃ | OCH₃ | " | — | " | cis-4-Methylcyclohexyloxy | |
| 118 | C₂H₅ | Cl | " | — | " | trans-4-Methylcyclohexyloxy | |
| 119 | CH₂OCH₃ | OCH₃ | " | — | " | trans-4-Methylcyclohexyloxy | |
| 120 | C₂H₅ | Cl | " | — | " | 1-Methylcyclohexyloxy | |
| 121 | CH₂OCH₃ | OCH₃ | " | — | " | 1-Methylcyclohexyloxy | |
| 122 | C₂H₅ | Cl | " | — | " | cis-4-tert-Butylcyclohexyloxy | |
| 123 | CH₂OCH₃ | OCH₃ | NH | — | cis | cis-4-tert-Butylcyclo- | |

5,691,321

TABLE 1-continued

| Ex. No. | R² | R³ | X | Y | Configuration on the cyclohexane | Z | M.p. [°C.] |
|---|---|---|---|---|---|---|---|
| 124 | C₂H₅ | Cl | " | — | " | trans-4-tert-Butylcyclohexyloxy | |
| 125 | CH₂OCH₃ | OCH₃ | " | — | " | trans-4-tert-Butylcyclohexyloxy | |
| 126 | C₂H₅ | Cl | " | — | " | cis-4-Phenylcyclohexyloxy | |
| 127 | CH₂OCH₃ | OCH₃ | " | — | " | cis-4-Phenylcyclohexyloxy | |
| 128 | C₂H₅ | Cl | " | — | " | trans-4-Phenylcyclohexyloxy | |
| 129 | CH₂OCH₃ | OCH₃ | " | — | " | trans-4-Phenylcyclohexyloxy | |
| 130 | C₂H₅ | Cl | NH | — | cis | 1-Methylcyclopentyloxy | Oil |
| 131 | CH₂OCH₃ | OCH₃ | " | — | " | 1-Methylcyclopentyloxy | |
| 132 | C₂H₅ | Cl | " | — | " | Cyclopropylmethyloxy | |
| 133 | CH₂OCH₃ | OCH₃ | " | — | " | Cyclopropylmethyloxy | |
| 134 | C₂H₅ | Cl | " | — | " | Cyclobutylmethyloxy | |
| 135 | CH₂OCH₃ | OCH₃ | " | — | " | " | |
| 136 | C₂H₅ | Cl | " | — | " | Cyclopentylmethyloxy | |
| 137 | CH₂OCH₃ | OCH₃ | " | — | " | Cyclopentylmethyloxy | |
| 138 | C₂H₅ | Cl | " | — | " | Cyclohexylmethyloxy | |
| 139 | CH₂OCH₃ | OCH₃ | " | — | " | " | |
| 140 | C₂H₅ | Cl | " | — | " | 1-Methylcyclobutyloxy | |
| 141 | CH₂OCH₃ | OCH₃ | " | — | " | " | |
| 142 | C₂H₅ | Cl | " | — | " | 1,2,3,4-Tetrahydronaphthalen-2-yloxy | |
| 143 | CH₂OCH₃ | OCH₃ | NH | — | cis | 1,2,3,4-Tetrahydronaphthalen-2-yloxy | |
| 144 | C₂H₅ | Cl | " | — | " | Decahydronaphthalen-2-yloxy | |
| 145 | CH₂OCH₃ | OCH₃ | " | — | " | Decahydronaphthalen-2-yloxy | |
| 146 | C₂H₅ | Cl | " | — | " | Indan-2-yloxy | |
| 147 | CH₂OCH₃ | OCH₃ | " | — | " | " | |
| 148 | C₂H₅ | Cl | " | — | " | Tetrahydrofuran-2-ylmethyloxy | |
| 149 | CH₂OCH₃ | OCH₃ | NH | — | cis | Tetrahydrofuran-2-ylmethyloxy | |
| 150 | C₂H₅ | Cl | " | — | " | Tetrahydropyran-2-ylmethyloxy | |
| 151 | " | " | " | — | " | 2-Thienylmethyloxy | |
| 152 | CH₂OCH₃ | OCH₃ | " | — | " | " | |
| 153 | C₂H₅ | Cl | " | — | " | —OCH₂Si(CH₃)₃ | |
| 154 | CH₂OCH₃ | OCH₃ | " | — | " | " | |
| 155 | C₂H₅ | Cl | " | — | " | O—(CH₂)₂Si(CH₃)₃ | |
| 156 | CH₂OCH₃ | OCH₃ | " | — | " | " | |
| 157 | C₂H₅ | Cl | " | — | " | —OC(CH₃)₂CF₃ | |
| 158 | CH₂OCH₃ | OCH₃ | " | — | " | " | |
| 159 | C₂H₅ | Cl | " | — | " | —OC(CH₃)₂CCl₃ | |
| 160 | CH₂OCH₃ | OCH₃ | " | — | " | " | |
| 161 | C₂H₅ | Cl | " | — | " | —OC(CH₃)₂COOCH₃ | |
| 162 | CH₂OCH₃ | OCH₃ | " | — | " | " | |
| 163 | C₂H₅ | Cl | " | — | " | —OC(CH₃)₂COCH₃ | |
| 164 | CH₂OCH₃ | OCH₃ | " | — | " | " | |
| 165 | C₂H₅ | Cl | NH | — | cis | —OC(CH₃)₂CH₂COCH₃ | |
| 166 | CH₂OCH₃ | OCH₃ | " | — | " | " | |
| 167 | C₂H₅ | Cl | " | — | " | —OCH(CH₃)₂COC₆H₅ | |
| 168 | CH₂OCH₃ | OCH₃ | " | — | " | " | |
| 169 | C₂H₅ | Cl | " | — | " | —OC(CH₃)₂C≡CH | |

TABLE 1-continued

| Ex. No. | R² | R³ | X | Y | Configuration on the cyclohexane | Z | M.p. [°C.] |
|---|---|---|---|---|---|---|---|
| 170 | CH₂OCH₃ | OCH₃ | NH | — | cis | —OC(CH₃)₂C≡CH | |
| 171 | C₂H₅ | Cl | " | — | " | OC(CH₃)₂C≡C—CH₃ | |
| 172 | CH₂OCH₃ | OCH₃ | " | — | " | " | |
| 173 | C₂H₅ | Cl | " | — | " | OC(CH₃)₂CH=CH₂ | |
| 174 | CH₂OCH₃ | OCH₃ | " | — | " | " | |
| 175 | C₂H₅ | Cl | " | — | " | OC(CH₃)₂CH₂—CH=CH₂ | |
| 176 | CH₂OCH₃ | OCH₃ | " | — | " | " | |
| 177 | C₂H₅ | Cl | " | — | " | —O—C(CH₃)₂—CH₂—C(CH₃)=CH₂ | |
| 178 | CH₂OCH₃ | OCH₃ | " | — | " | " | |
| 179 | C₂H₅ | Cl | " | — | " | —OC(CH₃)₂CH(CH₃)₂ | |
| 180 | CH₂OCH₃ | OCH₃ | " | — | " | " | |
| 181 | C₂H₅ | Cl | " | — | " | —OC(CH₃)₂CH₂(CH₃)₂ | |
| 182 | CH₂OCH₃ | OCH₃ | " | — | " | " | |
| 183 | C₂H₅ | Cl | " | — | " | —OC(CH₃)₂CH₂C(CH₃)₃ | |
| 184 | CH₂OCH₃ | OCH₃ | " | — | " | " | |
| 185 | C₂H₅ | Cl | " | — | " | —OC(CH₃)₂(CH₂)₃CH₃ | |
| 186 | CH₂OCH₃ | OCH₃ | " | — | " | " | |
| 187 | C₂H₅ | Cl | " | — | " | —OC(CH₃)₂(CH₂)₅CH₃ | |
| 188 | CH₂OCH₃ | OCH₃ | " | — | " | " | |
| 189 | C₂H₅ | Cl | " | — | " | —OC(CH₃)₂-cyclohexyl | |
| 190 | CH₂OCH₃ | OCH₃ | NH | — | cis | —OC(CH₃)₂-cyclohexyl | |
| 191 | C₂H₅ | Cl | NH | — | cis | —OC(CH₃)₂-cyclobutyl | |
| 192 | CH₂OCH₃ | OCH₃ | " | — | " | " | |
| 193 | C₂H₅ | Cl | " | — | " | —OC(CH₃)₂-cyclopropyl | |
| 194 | CH₂OCH₃ | OCH₃ | " | — | " | —OC(CH₃)₂-cyclopropyl | |
| 195 | C₂H₅ | Cl | " | — | " | —OC(CH₃)₂CH₂-cyclohexyl | |
| 196 | CH₂OCH₃ | OCH₃ | " | — | " | —OC(CH₃)₂CH₂-cyclohexyl | |
| 197 | C₂H₅ | Cl | " | — | " | —OC(CH₃)₂CH₂C₆H₅ | |
| 198 | CH₂OCH₃ | OCH₃ | " | — | " | " | |
| 199 | C₂H₅ | Cl | " | — | " | 1-(2-Furanyl)-1-methylethyloxy | |
| 200 | CH₂OCH₃ | OCH₃ | " | — | " | " | |
| 201 | C₂H₅ | Cl | NH | — | " | 1-(4-Biphenyl)-1-methylethyloxy | |
| 202 | CH₂OCH₃ | OCH₃ | " | — | " | 1-(4-Biphenyl)-1-methylethyloxy | |
| 203 | C₂H₅ | Cl | " | — | " | 1-(4-Fluorophenyl)-1-methylethyloxy | |
| 204 | CH₂OCH₃ | OCH₃ | " | — | " | 1-(4-Fluorophenyl)-1-methylethyloxy | |
| 205 | C₂H₅ | Cl | " | — | " | —OC(CH₃)₂-(4-isopropylphenyl) | |
| 206 | CH₂OCH₃ | OCH₃ | " | — | " | " | |
| 207 | C₂H₅ | Cl | " | O | " | C(CH₃)₃ | 93–95 |
| 208 | CH₂OCH₃ | OCH₃ | " | " | " | " | |
| 209 | C₂H₅ | Cl | O | " | " | " | 62 |
| 210 | CH₂OCH₃ | OCH₃ | O | O | cis | C(CH₃)₃ | |
| 211 | C₂H₅ | Cl | NH | " | " | Cyclohexyl | |
| 212 | CH₂OCH₃ | OCH₃ | " | " | " | " | |
| 213 | C₂H₅ | Cl | O | O | cis | Cyclohexyl | 50–54 |

TABLE 1-continued

| Ex. No. | R² | R³ | X | Y | Configuration on the cyclohexane | Z | M.p. [°C.] |
|---|---|---|---|---|---|---|---|
| 214 | " | " | NH | " | " | n-C₃H₇ | |
| 215 | CH₂OCH₃ | OCH₃ | " | " | " | " | |
| 216 | C₂H₅ | Cl | O | " | " | " | 61–63 |
| 217 | " | " | NH | " | " | CCl₃ | |
| 218 | CH₂OCH₃ | OCH₃ | " | " | " | " | |
| 219 | C₂H₅Cl | Cl | O | " | " | " | 96–97 |
| 220 | " | " | " | " | " | CH₃ | 65–68 |
| 221 | " | " | NH | " | " | C₆H₅ | |
| 222 | CH₂OCH₃ | OCH₃ | " | " | " | " | |
| 223 | C₂H₅ | Cl | O | " | " | " | 69–71 |
| 224 | " | " | NH | " | " | 4-tert-Butylphenyl | Oil |
| 225 | " | " | " | " | trans | " | 130–131 |
| 226 | " | " | NH | — | cis | —N(CH₃)(n-C₄H₉) | |
| 227 | CH₂OCH₃ | OCH₃ | " | — | " | " | |
| 228 | C₂H₅ | Cl | " | — | " | —N(CH₃)(n-C₈H₁₇) | |
| 229 | CH₂OCH₃ | OCH₃ | " | — | " | " | |
| 230 | C₂H₅ | Cl | " | — | " | —N(CH₃)(tert-C₄H₉) | |
| 231 | CH₂OCH₃ | OCH₃ | " | — | " | " | |
| 232 | C₂H₅ | Cl | " | — | " | Morpholino | |
| 233 | CH₂OCH₃ | OCH₃ | NH | — | cis | Morpholino | |
| 234 | C₂H₅ | Cl | " | — | " | 4-Phenylpiperidino | |
| 235 | CH₂OCH₃ | OCH₃ | " | — | " | " | |
| 236 | C₂H₅ | Cl | " | — | " | 4-Benzylpiperidino | Resin |
| 237 | CH₂OCH₃ | OCH₃ | " | — | " | " | |
| 238 | C₂H₅ | Cl | NH | — | cis | 2-(1,2,3,4-Tetra-hydroisoquinolyl) | 98–99 |
| 239 | CH₂OCH₃ | OCH₃ | " | — | " | 2-(1,2,3,4-Tetra-hydroisoquinolyl) | |
| 240 | C₂H₅ | Cl | " | — | " | —N(CH₃)C₆H₅ | 97–99 |
| 241 | CH₂OCH₃ | OCH₃ | " | — | " | " | |
| 242 | C₂H₅ | Cl | " | — | " | N-(4-tert-Butyl-phenyl)-N-methyl-amino | |
| 243 | CH₂OCH₃ | OCH₃ | " | — | " | N-(4-tert-Butyl-phenyl)-N-methyl-amino | |
| 244 | C₂H₅ | Cl | " | — | " | OH | 255° Dec. (Hydrochloride) |
| 245 | " | " | " | — | " | 4-tert-Butylphenyl | |
| 246 | " | " | " | — | " | 4-Trimethylsilyl-phenyl | |
| 247 | " | " | " | — | " | 4-Methoxyphenyl | |
| 248 | " | " | " | — | " | 4-Isopropyloxyphenyl | |
| 249 | " | " | " | — | " | 4-Fluorophenyl | |
| 250 | " | " | " | — | cis | 4-Trifluoromethyl-phenyl | |
| 251 | " | " | " | — | cis | N-(4-Methylphenyl)-N-methylamino | 118–120 |
| 252 | " | " | " | — | " | 1-(1,2,3,4-Tetra-hydroquinolyl) | 106–107 |

TABLE 2

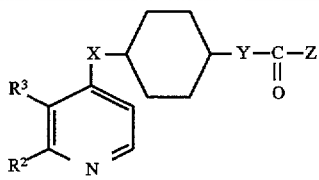

| Ex. No. | $R^2$ | $R^3$ | X | Y | Configuration on the cyclohexane | Z | M.p. [°C.] |
|---|---|---|---|---|---|---|---|
| 275 | $C_2H_5$ | Cl | NH | — | cis | H | |
| 276 | $C_2H_5$ | Cl | NH | — | cis | tert-Amyl | |
| 277 | $CH_2OCH_3$ | Cl | " | — | " | " | |
| 278 | $CH_2OCH_3$ | $OCH_3$ | " | — | " | " | |
| 279 | $C_2H_5$ | Br | " | — | " | " | |
| 280 | " | " | " | — | " | 2-Thienyl | |
| 281 | " | Cl | " | — | " | " | |
| 282 | $CH_2OCH_3$ | " | " | — | " | " | |
| 283 | " | $CH_3$ | " | — | " | " | |
| 284 | $C_2H_5$ | Cl | " | — | " | $C_6H_5$ | |
| 285 | " | Br | " | — | " | " | |
| 286 | $CH_2OCH_3$ | Cl | " | — | " | " | |
| 287 | " | $OCH_3$ | " | — | " | " | |
| 288 | $C_2H_5$ | Cl | " | — | " | 4-tert-Butylphenyl | |
| 289 | " | Br | " | — | " | " | |
| 290 | $CH_2OCH_3$ | $OCH_3$ | " | — | " | " | |
| 291 | " | " | " | — | " | " | |
| 292 | $C_2H_5$ | Cl | NH | — | cis | tert-Amyloxy | |
| 293 | " | Br | " | — | " | " | |
| 294 | $CH_2OCH_3$ | $OCH_3$ | " | — | " | " | |
| 295 | $CH_2OCH_3$ | Cl | NH | — | cis | " | |
| 296 | $C_2H_5$ | Cl | " | — | " | $C(CH_3)_2C_6H_5$ | |
| 297 | " | Br | " | — | " | " | |
| 298 | $CH_2OCH_3$ | $OCH_3$ | " | — | " | " | |
| 299 | " | Cl | " | — | " | " | |
| 300 | $C_2H_5$ | Cl | " | — | " | $OC(CH_3)_2(CH_2)_5CH_3$ | |
| 301 | " | Br | " | — | " | " | |
| 302 | $CH_2OCH_3$ | $OCH_3$ | " | — | " | " | |
| 303 | " | Cl | " | — | " | " | |
| 304 | $C_2H_5$ | Cl | " | — | " | $OC(CH_3)_2$-cyclohexyl | |
| 305 | " | Br | " | — | " | " | |
| 306 | $CH_2OCH_3$ | $OCH_3$ | " | — | " | " | |
| 307 | " | Cl | " | — | " | " | |
| 308 | $C_2H_5$ | Cl | " | — | " | $OC(CH_3)_2$-cyclopropyl | |
| 309 | " | Br | " | — | " | " | |
| 310 | $CH_2OCH_3$ | Cl | " | — | " | " | |
| 311 | " | $OCH_3$ | " | — | " | " | |
| 312 | $C_2H_5$ | Cl | " | — | " | $OC(CH_3)_2-CH=CH_2$ | |
| 313 | " | Br | " | — | " | " | |
| 314 | $CH_2OCH_3$ | $OCH_3$ | " | — | " | " | |
| 315 | $CH_2OCH_3$ | Cl | NH | — | cis | $OC(CH_3)_2CH=CH_2$ | |
| 316 | $C_2H_5$ | Cl | " | — | " | $OC(CH_3)_2C\equiv CH$ | |
| 317 | " | Br | " | — | " | " | |
| 318 | $CH_2OCH_3$ | $OCH_3$ | " | — | " | " | |
| 319 | " | Cl | " | — | " | " | |
| 320 | $C_2H_5$ | Cl | NH | — | cis | 4-Phenylpiperidino | |
| 321 | " | Br | " | — | " | " | |
| 322 | $CH_2OCH_3$ | $OCH_3$ | " | — | " | " | |
| 323 | " | " | " | — | " | " | |
| 324 | $C_2H_5$ | Cl | " | — | " | OH | |

TABLE 3

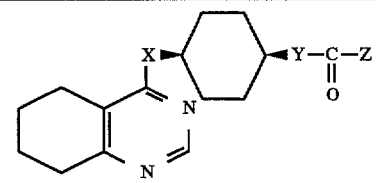

| Ex. No. | X | Y | Z | M.p. [°C.] |
|---|---|---|---|---|
| 325 | O | — | H | |
| 326 | " | — | CH₃ | |
| 327 | " | — | C(CH₃)₃ | |
| 328 | " | — | Phenyl | |
| 329 | " | — | 4-tert-Butylphenyl | |
| 330 | " | — | n-C₈H₁₇ | |
| 331 | " | — | —OC(CH₃)₃ | |
| 332 | " | — | —O(CH₂)₇CH₃ | |
| 333 | " | — | —OC(CH₃)₂C₆H₅ | |
| 334 | " | — | —OC(CH₃)₂(CH₂)₅CH₃ | |
| 335 | " | — | —OC(CH₃)₂-cyclohexyl | |
| 336 | " | — | —OC(CH₃)₂-cyclopropyl | |
| 337 | " | — | —OC(CH₃)₂CH=CH₂ | |
| 338 | " | — | —OC(CH₃)₂C≡CH | |
| 339 | O | — | 4-Phenylpiperidino | |
| 340 | " | — | 1-Methylcyclopentyloxy | |
| 341 | O | — | —OH | |
| 342 | " | — | —O—C(CH₃)₂CF₃ | |
| 343 | " | — | —OC(CH₃)₂CH₂C₆H₅ | |
| 344 | " | — | 2-(1,2,3,4-Tetrahydroiso-quinolyl) | |
| 345 | " | — | —N(CH₃)C₆H₅ | |
| 346 | " | — | 4-Benzylpiperidino | |

TABLE 4

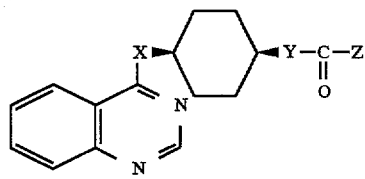

| Ex. No. | X | Y | Z | M.p. [°C.] |
|---|---|---|---|---|
| 350 | O | — | H | |
| 351 | NH | — | H | |
| 352 | O | — | CH₃ | |
| 353 | NH | — | CH₃ | |
| 354 | O | — | C(CH₃)₃ | |
| 355 | NH | — | " | |
| 356 | O | — | nC₈H₁₇ | |
| 357 | NH | — | " | |
| 358 | O | — | Phenyl | |
| 359 | NH | — | " | |
| 360 | O | — | 4-tert-Butylphenyl | |
| 361 | NH | — | " | |
| 362 | O | — | OC(CH₃)₃ | |
| 363 | NH | — | " | |
| 364 | O | — | O(CH₂)₇CH₃ | |
| 365 | NH | " | " | |
| 366 | O | — | —OC(CH₃)₂C₆H₅ | |
| 367 | NH | — | " | |
| 368 | O | — | —OC(CH₃)₂(CH₂)₅CH₃ | |
| 369 | NH | — | " | |
| 370 | O | — | —OC(CH₃)₂-cyclohexyl | |
| 371 | NH | — | " | |
| 371b | O | — | OC(CH₃)₂-cyclopropyl | |
| 372 | NH | — | " | |
| 373 | O | — | 1-Methylcyclohexyloxy | |
| 374 | NH | — | " | |
| 375 | O | — | 1-Methylcyclopentyloxy | |

TABLE 4-continued

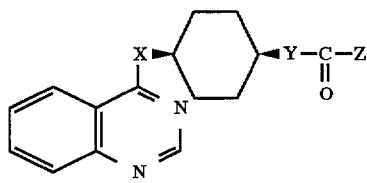

| Ex. No. | X | Y | Z | M.p. [°C.] |
|---|---|---|---|---|
| 376 | NH | — | " | |
| 377 | O | — | 1-Methylcyclobutyloxy | |
| 378 | NH | — | " | |
| 379 | O | — | 2-(1,2,3,4-Tetrahydro-naphthalen)yloxy | |
| 380 | NH | — | 2-(1,2,3,4-Tetrahydro-naphthalen)yloxy | |
| 381 | O | — | —O—C(CH₃)₂CF₃ | |
| 382 | NH | — | " | |
| 383 | O | — | —OC(CH₃)₂COOCH₃ | |
| 384 | NH | — | " | |
| 385 | O | — | —OC(CH₃)₂COCH₃ | |
| 386 | NH | — | " | |
| 387 | O | — | —OC(CH₃)₂COC₆H₅ | |
| 388 | NH | — | " | |
| 389 | O | — | O—C(CH₃)CH=CH₂ | |
| 390 | NH | — | " | |
| 391 | O | — | O—C(CH₃)₂C≡CH | |
| 392 | NH | — | " | |
| 393 | O | — | OC(CH₃)₂CH₂CH=CH₂ | |
| 394 | NH | — | " | |
| 395 | O | — | OC(CH₃)₂CH₂C₆H₅ | |
| 396 | NH | — | " | |
| 397 | O | — | OH | |
| 398 | NH | — | " | |
| 399 | O | — | —N(CH₃)C(CH₃)₃ | |
| 400 | NH | — | " | |
| 401 | O | — | —N(CH₃)n-C₈H₁₇ | |
| 402 | NH | — | " | |
| 403 | O | — | —N(CH₃)C₆H₅ | |
| 404 | NH | — | " | |
| 405 | O | — | N-(4-tert-Butylphenyl)-N-methylamino | |
| 406 | NH | — | N-(4-tert-Butylphenyl)-N-methylamino | |
| 407 | O | — | 2-(1,2,3,4-Tetrahydroiso-quinolin)yl | |
| 408 | NH | — | 2-(1,2,3,4-Tetrahydroiso-quinolin)yl | |
| 409 | O | — | 4-Phenylpiperidino | |
| 410 | NH | — | " | |
| 411 | O | — | 4-Benzylpiperidino | |
| 412 | NH | — | " | |

TABLE 5

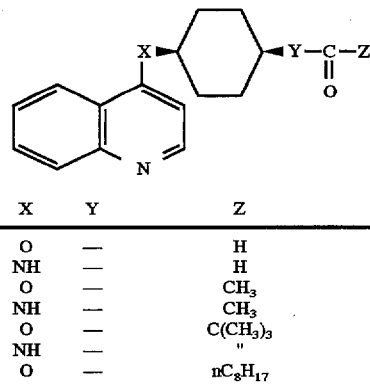

| Ex. No. | X | Y | Z | M.p. [°C.] |
|---|---|---|---|---|
| 421 | O | — | H | |
| 422 | NH | — | H | |
| 423 | O | — | CH₃ | |
| 424 | NH | — | CH₃ | |
| 425 | O | — | C(CH₃)₃ | |
| 426 | NH | — | " | |
| 427 | O | — | nC₈H₁₇ | |

TABLE 5-continued

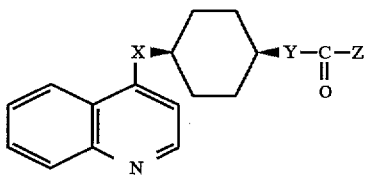

| Ex. No. | X | Y | Z | M.p. [°C.] |
|---|---|---|---|---|
| 428 | NH | — | " | |
| 429 | O | — | Phenyl | |
| 430 | NH | — | " | |
| 431 | O | — | 4-tert-Butylphenyl | |
| 432 | NH | — | " | |
| 433 | O | — | $OC(CH_3)_3$ | |
| 434 | NH | — | " | |
| 435 | O | — | $O(CH_2)_7CH_3$ | |
| 436 | NH | " | " | |
| 437 | O | — | $-OC(CH_3)_2C_6H_5$ | |
| 438 | NH | — | " | |
| 439 | O | — | $-OC(CH_3)_2(CH_2)_5CH_3$ | |
| 440 | NH | | " | |
| 441 | O | — | $-OC(CH_3)_2$-cyclohexyl | |
| 442 | NH | | " | |
| 443 | O | — | $OC(CH_3)_2$-cyclopropyl | |
| 444 | NH | | " | |
| 445 | O | — | 1-Methylcyclohexyloxy | |
| 446 | NH | — | " | |
| 447 | O | — | 1-Methylcyclopentyloxy | |
| 448 | NH | — | " | |
| 449 | O | — | 1-Methylcyclobutyloxy | |
| 450 | NH | — | " | |
| 451 | O | — | 2-(1,2,3,4-Tetrahydro-naphthalen)yloxy | |
| 452 | NH | — | 2-(1,2,3,4-Tetrahydro-naphthalen)yloxy | |
| 453 | O | — | $-O-C(CH_3)_2CF_3$ | |
| 454 | NH | — | " | |
| 455 | O | — | $-OC(CH_3)_2COOCH_3$ | |
| 456 | NH | — | " | |
| 457 | O | — | $-OC(CH_3)_2COCH_3$ | |
| 458 | NH | — | " | |
| 459 | O | — | $-OC(CH_3)_2COC_6H_5$ | |
| 460 | NH | — | " | |
| 461 | O | — | $O-C(CH_3)CH=CH_2$ | |
| 462 | NH | — | " | |
| 463 | O | — | $O-C(CH_3)_2C\equiv CH$ | |
| 464 | NH | — | " | |
| 465 | O | — | $OC(CH_3)_2CH_2CH=CH_2$ | |
| 466 | NH | — | " | |
| 467 | O | — | $OC(CH_3)_2CH_2C_6H_5$ | |
| 468 | NH | — | " | |
| 469 | O | — | OH | |
| 470 | NH | — | " | |
| 471 | O | — | $-N(CH_3)C(CH_3)_3$ | |
| 472 | NH | — | " | |
| 473 | O | — | $-N(CH_3)n-C_8H_{17}$ | |
| 474 | N | — | " | |
| 475 | O | — | $-N(CH_3)C_6H_5$ | |
| 476 | NH | — | " | |
| 477 | O | — | N-(4-tert-Butylphenyl)-N-methylamino | |
| 478 | NH | — | N-(4-tert-Butylphenyl)-N-methylamino | |
| 479 | O | — | 2-(1,2,3,4-Tetrahydroiso-quinolin)yl | |
| 480 | NH | — | 2-(1,2,3,4-Tetrahydroiso-quinolin)yl | |
| 481 | O | — | 4-Phenylpiperidino | |
| 482 | NH | — | " | |
| 483 | O | — | 4-Benzylpiperidino | |
| 484 | NH | — | " | |

TABLE 6

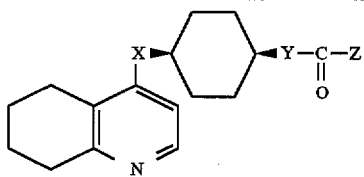

| Ex. No. | X | Y | Z | M.p. [°C.] |
|---|---|---|---|---|
| 521 | O | — | H | |
| 522 | NH | — | H | |
| 523 | O | — | $CH_3$ | |
| 524 | NH | — | $CH_3$ | |
| 525 | O | — | $C(CH_3)_3$ | |
| 526 | NH | — | " | |
| 527 | O | — | $nC_8H_{17}$ | |
| 528 | NH | — | " | |
| 529 | O | — | Phenyl | |
| 530 | NH | — | " | |
| 531 | O | — | 4-tert.Butylphenyl | |
| 532 | NH | — | " | |
| 533 | O | — | $OC(CH_3)_3$ | |
| 534 | NH | — | " | |
| 535 | O | — | $O(CH_2)_7CH_3$ | |
| 536 | NH | " | " | |
| 537 | O | — | $-OC(CH_3)_2C_6H_5$ | |
| 538 | NH | | " | |
| 539 | O | — | $-OC(CH_3)_2(CH_2)_5CH_3$ | |
| 540 | NH | | " | |
| 541 | O | — | $-OC(CH_3)_2$-cyclohexyl | |
| 542 | NH | | " | |
| 543 | O | — | $OC(CH_3)_2$-cyclopropyl | |
| 544 | NH | | " | |
| 545 | O | — | 1-Methylcyclohexyloxy | |
| 546 | NH | — | " | |
| 547 | O | — | 1-Methylcyclopentyloxy | |
| 548 | NH | — | " | |
| 549 | O | — | 1-Methylcyclobutyloxy | |
| 550 | NH | — | " | |
| 551 | O | — | 2-(1,2,3,4-Tetrahydro-naphthalen)yloxy | |
| 552 | NH | — | 2-(1,2,3,4-Tetrahydro-naphthalen)yloxy | |
| 553 | O | — | $-O-C(CH_3)_2CF_3$ | |
| 554 | NH | — | " | |
| 555 | O | — | $-OC(CH_3)_2COOCH_3$ | |
| 556 | NH | — | " | |
| 557 | O | — | $-OC(CH_3)_2COCH_3$ | |
| 558 | NH | — | " | |
| 559 | O | — | $-OC(CH_3)_2COC_6H_5$ | |
| 560 | NH | — | " | |
| 561 | O | — | $O-C(CH_3)CH=CH_2$ | |
| 562 | NH | — | " | |
| 563 | O | — | $O-C(CH_3)_2C\equiv CH$ | |
| 564 | NH | — | " | |
| 565 | O | — | $OC(CH_3)_2CH_2CH=CH_2$ | |
| 566 | NH | — | " | |
| 567 | O | — | $OC(CH_3)_2CH_2C_6H_5$ | |
| 568 | NH | — | " | |
| 569 | O | — | OH | |
| 570 | NH | — | " | |
| 571 | O | — | $-N(CH_3)C(CH_3)_3$ | |
| 572 | NH | — | " | |
| 573 | O | — | $-N(CH_3)n-C_8H_{17}$ | |
| 574 | NH | — | " | |
| 575 | O | — | $-N(CH_3)C_6H_5$ | |
| 576 | NH | — | " | |
| 577 | O | — | N-(4-tert-Butylphenyl)-N-methylamino | |
| 578 | NH | — | N-(4-tert-Butylphenyl)-N-methylamino | |
| 579 | O | — | 2-(1,2,3,4-Tetrahydroiso-quinolin)yl | |
| 580 | NH | — | 2-(1,2,3,4-Tetrahydroiso-quinolin)yl | |
| 581 | O | — | 4-Phenylpiperidino | |

TABLE 6-continued

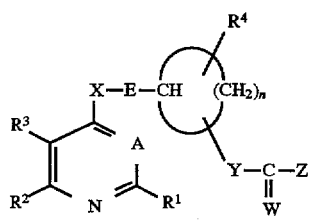

| Ex. No. | X | Y | Z | M.p. [°C.] |
|---|---|---|---|---|
| 582 | NH | — | " | |
| 583 | O | — | 4-Benzylpiperidino | |
| 584 | NH | — | " | |

We claim:

1. A compound of the formula I

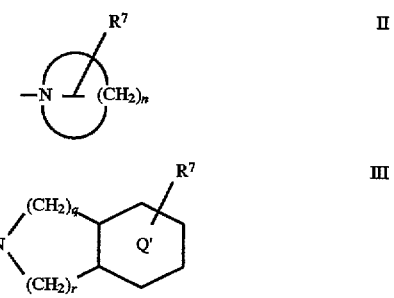

in which $R^1$ is hydrogen, halogen, $(C_1-C_4)$-alkyl or $(C_3-C_5)$-cycloalkyl;

$R^2$ and $R^3$ are identical or different and are in each case hydrogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_1-C_4)$-haloalkoxy, $(C_1-C_4)$-alkoxy-$(C_1-C_4)$-alkyl, $(C_1-C_4)$-haloalkoxy-$(C_1-C_4)$-alkyl, $(C_1-C_4)$-alkoxy-$(C_1-C_4)$-haloalkyl, $(C_1-C_4)$-haloalkoxy-$(C_1-C_4)$-haloalkyl, halogen, hydroxyl, $(C_1-C_4)$-hydroxyalkayl, $(C_1-C_4)$-alkanoyl, $(C_1-C_4)$-alkanoyl-$(C_1-C_4)$-alkyl, $(C_1-C_4)$-haloalkanoyl, $(C_3-C_5)$-cycloalkyl, $(C_3-C_5)$-halocycloalkyl, cyano, $(C_1-C_4)$-cyanoalkyl, nitro, $(C_1-C_4)$-nitroalkyl,1 thiocyano, $(C_1-C_4)$-alkoxycarbonyl, $(C_1-C_4)$-alkoxycarbonyl-$(C_1-C_4)$-alkyl, $(C_1-C_4)$-haloalkoxycarbonyl, $(C_1-C_4)$-alkylthio, $(C_1-C_4)$-alkylthio-$(C_1-C_4)$-alkyl, $(C_1-C_4)$-haloalkylthio, $(C_1-C_4)$-alkylsulfinyl, $(C_1-C_4)$-haloalkaylsulfinyl, $(C_1-C_4)$-alkylsulfonyl or $(C_1-C_4)$-haloalkylsulfony;

X is NH, oxygen or sulfur;

E is a direct bond or a straight-chain or branched $(C_1-C_4)$-alkanediyl group;

n is an integer from 2 to 7;

$R^4$ is hydrogen or $(C_1-C_4)$-alkyl;

Y is oxygen or a direct bond;

W is oxygen or sulfur;

Z is a radical $DR^5$ or $NR^5R^6$;

D is oxygen, sulfur or a direct bond;

$R^5$ and $R^6$ are identical or different and are hydrogen, hydroxyl, cyano, thiocyano, nito, halogen alkyl, alkenyl, alkynyl, aryl or heterocyclyl, it being possible for the aryl or heterocyclyl radicals mentioned to be unsubstituted or to have attached to them up to three, in the case of fluorine also up to the maximum number of, identical or different radicals and it being possible for one or more nonadjacent saturated carbon units in the abovementioned alkyl, alkenyl or alkynyl radicals to be replaced by a carbonyl group or by hetero atom units, $S(O)_x$, where x=0, 1 or 2, $NR^9$ or $SiR^7R^8$, $R^9$ being hydrogen, $(C_1-C_4)$-alkyl, $(C_1-C_4)$-alkoxy or $(C_1-C_4)$-alkanoyl and $R^7$ and $R^8$ being $(C_1-C_4)$-alkyl; and in which moreover 3 to 12 atoms of these hydrocarbon radicals which are optionally modified as above can form a cycle and it is possible for these hydrocarbon radicals, with or without the abovementioned variations, to be optionally substituted by one or more in the case of fluorine up to the maximum number of, identical or different radicals selected from the series consisting of halogen, aryl, aryloxy, arylthio, cycloalkoxy, cycloalkylthio, heterocyclyl, heterocyclyloxy, heterocyclythio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoqloxy, aroyloxy, arylakanoyloxy, heterocyclylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, $R^5$ and $R^6$ form a ring system of the formula II or III $$\text{II, III structures}$$

in which the six-membered ring Q' is saturated or aromatic;

m is an integer from 2 to 7;

q and r are zero or integers whose total is a number from 2 to 4 and in which one $CH_2$ unit is optionally replaced by oxygen, sulfur or a group $NR^8$, and $R^7$ and $R^8$ are identical or different and are in each case hydrogen, alkyl, haloalkyl, alkoxy, alkylthio, phenylalkyl or phenyl and the phenyl groups can be unsubstituted or have attached to them up to three, in the case of fluorine also up to the maximum number of, identical or different substituents, wherein a heterocyclyl is a heteroaromatic or heteroaliphatic ring system, a heteroaromatic ring system is a $(C_6-C_{14})$-aryl radical in which at least one CH group is replaced by N and/or at least two adjacent CH groups are replaced by S, NH or O, a heteroaliphatic ring system is $(C_3-C_8)$-cycloalkyl in which at least one carbon unit is replaced by O, S or $NR^{11}$, and $R^{11}$ is $(C_1-C_4)$-alkyl, $(C_1-C_4)$-alkoxy or $(C_6-C_{14})$-aryl, or salts thereof.

2. A compound of the formula I according to claim 1

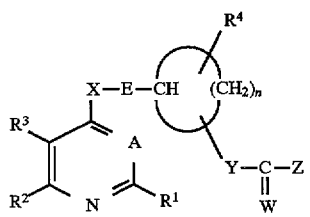

in which

R¹ is hydrogen, halogen, (C₁–C₄)-alkyl or (C₃–C₅)-cycloalkyl;

R² and R³ are identical or different and are in each case hydrogen, (C₁–C₄)-alkyl, (C₁–C₄)-haloalkyl, (C₂–C₄)-alkenyl, (C₂–C₄)-haloalkenyl, (C₂–C₄)-alkynyl, (C₂–C₄)-haloalkynyl, (C₁–C₄)-alkoxy, (C₁–C₄)-haloalkoxy, (C₁–C₄)-alkoxy-(C₁–C₄)-alkyl, (C₁–C₄)-haloalkoxy-(C₁–C₄)-alkyl, (C₁–C₄)-alkoxy-(C₁–C₄)-haloalkyl, (C₁–C₄)-haloalkoxy-(C₁–C₄)-haloalkyl, halogen, hydroxyl, (C₁–C₄)-hydroxyalkyl, (C₁–C₄)-alkanoyl, (C₁–C₄)-alkanoyl-(C₁–C₄)-alkyl, (C₁–C₄)-haloalkanoyl, (C₃–C₅)-cycloalkyl, (C₃–C₅)-halocycloalkyl, cyano, (C₁–C₄)-cyanoalkyl, nitro, (C₁–C₄)-nitroalkyl, thiocyano, (C₁–C₄)-alkoxycarbonyl, (C₁–C₄)-alkoxycarbonyl-(C₁–C₄)-alkyl, (C₁C₄)-haloalkoxycarbonyl, (C₁–C₄)-alkylthio, (C₁–C₄)-alkylthio-(C₁–C₄)-alkyl, (C₁–C₄)-haloalkylthio, (C₁–C₄)-alkylsulfinyl, (C₁–C₄)-haloalkylsulfinyl, (C₁–C₄)-alkylsulfonyl or (C₁–C₄)-haloalkylsulfonyl;

is N;

X is NH, oxygen or sulfur;

E is a direct bond or a straight-chain or branched (C₁–C₄) -alkanediyl group;

n is an integer from 2 to 7;

R⁴ is hydrogen or (C₁–C₄)-alkyl;

Y is oxygen or a direct bond;

W is oxygen or sulfur;

Z is a radical DR⁵ or NR⁵R⁶;

D is oxygen, sulfur or a direct bond:

R⁵ and R⁶ are identical or different and are hydrogen, alkyl, alkenyl, alkynyl, aryl or heterocyclyl, it being possible for the aryl or heterocyclyl radicals mentioned to be unsubstituted or to have attached to them up to three, in the case of fluorine also up to the maximum number of, identical or different radicals and it being possible for one or more nonadjacent saturated carbon units in the above-mentioned alkyl, alkenyl or alkynyl radicals to be replaced by a carbonyl group or by hetero atom units, $S(O)_x$, where x=0, 1 or 2, $NR^9$ or $SiR^7R^8$, R⁹ being hydrogen, (C₁–C₄)-alkyl, (C₁–C₄)-alkoxy or (C₁–C₄)-alkanoyl and R⁷ and R⁸ being (C₁–C₄)-alkyl; and in which moreover 3 to 12 atoms of these hydrocarbon radicals which are optionally modified as above can form a cycle and it is possible for these hydrocarbon radicals, with or without the above-mentioned variations, to be optionally substituted by one or more in the case of fluorine up to the maximum number of, identical or different radicals selected from the series consisting of halogen, aryl, aryloxy, arylthio, cycloalkoxy, cycloalkylthio, heterocyclyl, heterocyclyloxy, heterocyclylthio, alkanoyl, cycloalkanoyl, haloalkanoyl, aroyl, arylalkanoyl, cycloalkylalkanoyl, heterocyclylalkanoyl, alkoxycarbonyl, haloalkoxycarbonyl, cycloalkoxycarbonyl, cycloalkylalkoxycarbonyl, arylalkoxycarbonyl, heterocyclylalkoxycarbonyl, aryloxycarbonyl, heterocyclyloxycarbonyl, alkanoyloxy, haloalkanoyloxy, cycloalkanoyloxy, cycloalkylalkanoyloxy, aroyloxy, arylalkanoyloxy, heterocyclylalkanoyloxy, alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, R⁵ and R⁶ form a ring system of the formula II or III

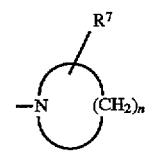

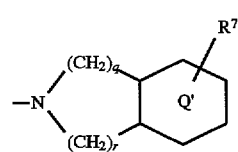

in which the six-membered ring Q' is saturated or aromatic;

m is an integer from 2 to 7;

q and r are zero or integers whose total is a number from 2 to 4 and in which one CH₂ unit is optionally replaced by oxygen, sulfur or a group NR⁸, and R⁷ and R⁸ are identical or different and are in each case hydrogen, alkyl, haloalkyl, alkoxy, alkylthio, phenylalkyl or phenyl and the phenyl groups can be unsubstituted or have attached to them up to three, in the case of fluorine also up to the maximum number of, identical or different substituents, wherein a heterocyclyl is a heteroaromatic or heteroaliphatic ring system, a heteroaromatic ring system is a (C₆–C₄)-aryl radical in which at least one CH group is replaced by N and/or at least two adjacent CH groups are replaced by S, NH or O, a heteroaliphatic ring system is (C₃–C₈)-cycloalkyl in which at least one carbon unit is replaced by O, S or NR¹¹, and is (C₁–C₄)-alkyl, (C₁–C₄)-alkoxy or (C₆–C₁₄)-aryl, or salts thereof.

3. A compound of the formula I as claimed in claim 1, in which R⁵ and R⁶ are hydrogen, (C₁–C₂₀)-alkyl, (C₂–C₂₀)-alkenyl, (C₂–C₂₀)-alkynyl, aryl, heterocyclyl, hydroxyl, cyano, thiocyano, nitro or halogen, it being possible for the aryl or heterocyclyl radicals mentioned to be unsubstituted or to have attached to them up to three, in the case of fluorine also up to the maximum number of, identical or different radicals and it being possible for one or more, nonadjacent saturated carbon units in the abovementioned alkyl, alkenyl or alkynyl radicals to be replaced by a carbonyl group or by hetero atom units, $S(O)_x$, where x is 0, 1 or 2, $NR^6$ or $SiR^7R^8$, R⁹ being hydrogen, (C₁–C₄)-alkyl, (C₁–C₄)-alkoxy or (C₁–C₄)-alkanoyl and R⁷ and R⁸ being (C₁–C₄)-alkyl; and in which furthermore 3 to 12 atoms of these hydrocarbon radicals which are optionally modified as above can form a cycle and it is possible for these hydrocarbon radicals, with or without the abovementioned variations, to be optionally substituted by one or more in the case of halogen up to the maximum number of, identical or different radicals selected from the series consisting of halogen, aryl, aryloxy, arylthio, $(C_3-C_8)$-cycloalkoxy, $(C_3-C_8)$-cycloalkyltho, heterocyclyl, heterocyclyloxy, heterocyclylthio, $(C_1-C_{20})$-alkanoyl, $(C_3-C_8)$-cycloalkanoyl, $(C_1-C_{20})$-haloalkanoyl, aroyl, aryl-$(C_1-C_4)$-alkanoyl, $(C_3-C_8)$-cycloalkyl-$(C_1-C_4)$-alkanoyl, heterocyclyl-$(C_1-C_4)$-alkanoyl, $(C_1-C_{20})$-alkoxycarbonyl, $(C_1-C_{20})$-haloalkoxycarbonyl, $(C_3-C_8)$-cycloalkoxycarbonyl, $(C_3-C_8)$-cycloalkyl-$(C_1-C_4)$-alkoxycarbonyl, aryl-$(C_1-C_4)$-alkoxycarbonyl, heterocyclyl-$(C_1-C_4)$-alkoxycarbonyl, aryloxycarbonyl, heterocyclyloxycarbonyl, $(C_1-C_{20})$-alkanoyloxy, $(C_2-C_{20})$-haloalkanoylalkoxy, $(C_3-C_8)$-cycloalkanoyloxy, $(C_3-C_8)$-cycloalkyl-$(C_1-C_4)$-alkanoyloxy, aroyloxy, aryl-$(C_1-C_4)$-alkanoyloxy, heterocyclyl-$(C_1-C_4)$-alkanoyloxy, $(C_1-C_{20})$-alkylsulfonyloxy, arylsulfonyloxy, hydroxyl, cyano, thiocyano or nitro, it being possible for the cycloaliphatic, aromatic or heterocyclic ring systems amongst the substituents which have just been mentioned to be unsubstituted or to have attached to them up to three, in the case of fluorine also up to the maximum number of, identical or different substituents, or $R^5$ and $R^6$ form a ring system of the formula II or III in which the six-membered ring Q' is saturated or aromatic;

m is an integer from 2 to 7;

q and r are integers whose total is a number from 2 to 4 and in which one $CH_2$ unit can optionally be replaced by oxygen, sulfur or a group $NR^{10}$, and $R^7$ and $R^8$ are identical or different and are in each case hydrogen, $(C_1-C_8)$-alkyl, $(C_1-C_4)$-haloalkyl, $(C_1-C_4)$-alkoxy, $(C_1-C_4)$-alkylthio or phenyl-$(C_1-C_4)$-alkyl, or can have attached to them up to three, in the case of fluorine also up to the maximum number of, identical or different substituents, or salts thereof.

4. A compound of the formula I as claimed in claim 1, in which $R^1$ is hydrogen;

$R^2$ is $(C_1-C_4)$-alkyl, cyclopropyl, $(C_1-C_4)$-haloalkyl or methoxymethyl;

$R^3$ is hydrogen, methyl, ethyl, methoxy, ethoxy, halogen or cyano;

A is N;

X is NH or oxygen;

E is a direct bond;

$R^4$ is hydrogen or $(C_1-C_4)$-alkyl;

Y is oxygen or a direct bond;

W is oxygen;

Z is a radical $DR^5$ or $NR^5R^6$; and

D is oxygen or a direct bond;

or salts thereof.

5. A compound of the formula I as claimed in claim 1, in which $R^2$ is $(C_1-C_3)$-alkyl, cyclopropyl, trifluoromethyl or methoxymethyl;

$R^3$ is methyl, ethyl, methoxy, halogen or cyano; and

Z is a radical $DR^5$ or $NR^5R^6$;

or salts thereof.

6. A compound of the formula I as claimed in claim 1, in which $R^1$ is hydrogen;

$R^2$ is ethyl, propyl, isopropyl or methoxymethyl;

$R^3$ is fluorine, chlorine, bromine or methoxy;

A is N;

X is NH;

E is a direct bonds $R^4$ is hydrogen;

n is the number 4 or 5;

Y is oxygen or a direct bonds

Z is $DR^5$ or $NR^5R^6$;

D is oxygen or a direct bond, and

W is oxygen;

or salts thereof.

7. A compound of the formula I as claimed in claim 1, in which $R^1$ is hydrogen;

$R^2$ is methoxymethyl and $R^3$ is methoxy or chlorine; or $R^2$ is ethyl, propyl or isopropyl and $R^3$ is chlorine or bromine;

A is N;

X is NH;

E is a direct bond;

$R^4$ is hydrogen;

n is the number 4 or 5;

Y is a direct bond;

Z is $DR^5$ or $NR^5R^6$;

D is oxygen or a direct bond, and

W is oxygen;

or salts thereof.

8. A compound of the formula I as claimed in claim 1, in which $R^1$ is hydrogen;

is methoxymethyl and $R^3$ is methoxy; or $R^2$ is ethyl and $R^3$ is chlorine or bromine;

A is nitrogen;

X is NH;

E is a direct bond;

$R^4$ is hydrogen;

is the number 5 and the radicals are in the 1,4 position and in the cis position relative to each other;

Y is a direct bond;

W is oxygen;

Z is $DR^5$;

D is oxygen or a direct bond;

or salts thereof.

9. A compound of the formula I as claimed in claim 1, in which n is 5, —Y—CW—Z is in the 4 position of the cyclohexane ring relative to —X—E— and these two groups are in the cis configuration to each other, or salts thereof.

10. A composition comprising at least one compound as claimed in claim 1 and at least one formulation agent.

11. A fungicidal composition as claimed in claim 10, comprising a fungicidally effective amount of at least one compound as claimed in claim 1 together with the additives or auxiliaries which are conventional for this application.

12. An insecticidal, acaricidal, ixodicidal or nematicidal composition comprising an effective amount of at least one compound as claimed in claim 1 and further comprising at least one formulation agent together with the additives or auxiliaries conventional for this application.

13. A crop protection product comprising a fungicidally, insecticidally, acaricidally, ixodicidally or nematicidally effective amount of at least one compound as claimed in claim 1 and at least one further active substance, from the series of the fungicides, insecticides, attractants, sterilants, acaricides, nematicides and herbicides, together with the auxiliaries and additives conventional for this application.

14. A method of controlling endoparasites or ectoparasites, which comprises administering an amount of a compound as claimed in claim 1 which is effective for such an application.

15. A method of controlling phytopathogenic fungi, which comprises applying a fungicidally effective amount of a compound as claimed in claim 1 to these fungi or to the plants, areas or substrates contaminated with them, or to seed.

16. A method of controlling insect pests, Acarina, molluscs and nematodes, in which an effective amount of a compound as claimed in claim 1 is applied to these insect pests, Acarina, molluscs and nematodes, or to the plants, areas or substrates infested with them.

* * * * *

UNITED STATES PATENT AND TRADEMARK OFFICE
CERTIFICATE OF CORRECTION

PATENT NO.   : 5,691,321
DATED        : November 25, 1997
INVENTOR(S)  : SCHAPER et al.

It is certified that error appears in the above-identified patent and that said Letters Patent is hereby corrected as shown below:

IN THE CLAIMS:

Claim 1, column 49, after line 49, insert --A is N;--

Claim 2, column 51, line 33, change "is N" to --A is N--

Signed and Sealed this

Twenty-first Day of March, 2000

Attest:

Attesting Officer

Q. TODD DICKINSON

Commissioner of Patents and Trademarks